United States Patent
Chen

(10) Patent No.: US 11,780,917 B2
(45) Date of Patent: Oct. 10, 2023

(54) ANTI-GM2AP ANTIBODY AND APPLICATIONS THEREOF

(71) Applicant: Taiwan Innovative Integration services Co., Ltd., Taipei (TW)

(72) Inventor: Shui-Tein Chen, Taipei (TW)

(73) Assignee: Taiwan Innovative Integration services Co., Ltd., Taipei (TW)

( * ) Notice: Subject to any disclaimer, the term of this patent is extended or adjusted under 35 U.S.C. 154(b) by 50 days.

(21) Appl. No.: 17/402,619

(22) Filed: Aug. 16, 2021

(65) Prior Publication Data

US 2023/0073083 A1    Mar. 9, 2023

(51) Int. Cl.
C07K 16/28    (2006.01)
G01N 33/68    (2006.01)

(52) U.S. Cl.
CPC ..... *C07K 16/2803* (2013.01); *G01N 33/6857* (2013.01); *C07K 2317/52* (2013.01); *C07K 2317/565* (2013.01)

(58) Field of Classification Search
CPC ............ C07K 16/2803; C07K 2317/52; C07K 2317/565; G01N 33/6857
See application file for complete search history.

(56) References Cited

U.S. PATENT DOCUMENTS

| 7,510,843 | B2 | 3/2009 | Roecklin et al. | |
|---|---|---|---|---|
| 2007/0065881 | A1* | 3/2007 | Perron | C07K 14/705 435/7.2 |

FOREIGN PATENT DOCUMENTS

CN    1352114 A    6/2002

OTHER PUBLICATIONS

McCarthy et al. (J. Immunol. Methods, 251(1-2): 137-149, 2001) (Year: 2001).*
"GM2A monoclonal antibody (M02), clone 2C8", Abnova, (Jun. 20, 2021), URL: https://www.abnova.com/products/products_detail.asp?catalog_id=H00002760-M02, XP093012297, the whole document.
"GM2A Monoclonal antibody Catalog No. 66080-1-Ig", proteintech, (Nov. 8, 2019), URL: https://www.ptglab.com/products/GM2A-Antibody-66080-1-Ig.htm, (Jan. 9, 2023), XP093012307, the whole document, in particular, p. 1.
"GM2A antibody", NovoPro, (Jan. 15, 2020), URL: https://novoprolabs.com/p/gm2a-antibody-107302.html, (Jan. 9, 2023), XP093012329, the whole document.

* cited by examiner

*Primary Examiner* — Daniel E Kolker
*Assistant Examiner* — Ashley H. Gao
(74) *Attorney, Agent, or Firm* — Huan Yi Lin

(57) ABSTRACT

The present disclosure disclosed herein a recombinant antibody or the antigen-binding fragment thereof which specifically binds GM2-activator protein (GM2AP). The recombinant antibody or the antigen-binding fragment thereof comprises a light chain variable region (LCVR) comprising three light chain complementary determining regions (LCDR1-3) amino acid sequences and a heavy chain variable region (HCVR) comprising three heavy chain complementary determining regions (HCDR1-3) set forth in the sequences disclosed in the embodiments of the present application. Polynucleotides encoding the same, vectors, host cells, kits and methods for detecting GM2AP and methods for inducing these recombinant antibodies or the antigen-binding fragment thereof are also provided.

14 Claims, 5 Drawing Sheets

Specification includes a Sequence Listing.

(A)

(B)

SEQUENCE LISTING

```
<160> NUMBER OF SEQ ID NOS: 119

<210> SEQ ID NO 1
<211> LENGTH: 14
<212> TYPE: PRT
<213> ORGANISM: Artificial Sequence
<220> FEATURE:
<223> OTHER INFORMATION: GM2AP and one of the amino acids from position
      1 to 14 is glycosylated with (GlcNAc)2Fuc(Man)3

<400> SEQUENCE: 1

Pro Ile Ile Val Pro Gly Asn Val Thr Leu Ser Val Val Gly
1               5                   10

<210> SEQ ID NO 2
<211> LENGTH: 193
<212> TYPE: PRT
<213> ORGANISM: Artificial Sequence
<220> FEATURE:
<223> OTHER INFORMATION: GM2AP and one of the amino acids from position
      57 to 70 is glycosylated with (GlcNAc)2Fuc(Man)3

<400> SEQUENCE: 2

Met Gln Ser Leu Met Gln Ala Pro Leu Leu Ile Ala Leu Gly Leu Leu
1               5                   10                  15

Leu Ala Ala Pro Ala Gln Ala His Leu Lys Lys Pro Ser Gln Leu Ser
                20                  25                  30

Ser Phe Ser Trp Asp Asn Cys Asp Glu Gly Lys Asp Pro Ala Val Ile
            35                  40                  45

Arg Ser Leu Thr Leu Glu Pro Asp Pro Ile Ile Val Pro Gly Asn Val
        50                  55                  60

Thr Leu Ser Val Met Gly Ser Thr Ser Val Pro Leu Ser Ser Pro Leu
65                  70                  75                  80

Lys Val Asp Leu Val Leu Glu Lys Glu Val Ala Gly Leu Trp Ile Lys
                85                  90                  95
```

```
Ile Pro Cys Thr Asp Tyr Ile Gly Ser Cys Thr Phe Glu His Phe Cys
            100                 105                 110

Asp Val Leu Asp Met Leu Ile Pro Thr Gly Glu Pro Cys Pro Glu Pro
            115                 120                 125

Leu Arg Thr Tyr Gly Leu Pro Cys His Cys Pro Phe Lys Glu Gly Thr
            130                 135                 140

Tyr Ser Leu Pro Lys Ser Glu Phe Val Val Pro Asp Leu Glu Leu Pro
145                 150                 155                 160

Ser Trp Leu Thr Thr Gly Asn Tyr Arg Ile Glu Ser Val Leu Ser Ser
                165                 170                 175

Ser Gly Lys Arg Leu Gly Cys Ile Lys Ile Ala Ala Ser Leu Lys Gly
            180                 185                 190

Ile

<210> SEQ ID NO 3
<211> LENGTH: 193
<212> TYPE: PRT
<213> ORGANISM: Artificial Sequence
<220> FEATURE:
<223> OTHER INFORMATION: GM2AP and one of the amino acids from position
      57 to 70 is glycosylated with (GlcNAc)2Fuc(Man)3

<400> SEQUENCE: 3

Met Gln Ser Leu Met Gln Ala Pro Leu Leu Ile Ala Leu Gly Leu Leu
1               5                   10                  15

Leu Ala Ala Pro Ala Gln Ala His Leu Lys Lys Pro Ser Gln Leu Ser
            20                  25                  30

Ser Phe Ser Trp Asp Asn Cys Asp Glu Gly Lys Asp Pro Ala Val Ile
            35                  40                  45

Arg Ser Leu Thr Leu Glu Pro Asp Pro Ile Ile Val Pro Gly Asn Val
50                  55                  60

Thr Leu Ser Val Val Gly Ser Thr Ser Val Pro Leu Ser Ser Pro Leu
65                  70                  75                  80

Lys Val Asp Leu Val Leu Glu Lys Glu Val Ala Gly Leu Trp Ile Lys
            85                  90                  95

Ile Pro Cys Thr Asp Tyr Ile Gly Ser Cys Thr Phe Glu His Phe Cys
            100                 105                 110

Asp Val Leu Asp Met Leu Ile Pro Thr Gly Glu Pro Cys Pro Glu Pro
            115                 120                 125

Leu Arg Thr Tyr Gly Leu Pro Cys His Cys Pro Phe Lys Glu Gly Thr
            130                 135                 140

Tyr Ser Leu Pro Lys Ser Glu Phe Val Val Pro Asp Leu Glu Leu Pro
145                 150                 155                 160

Ser Trp Leu Thr Thr Gly Asn Tyr Arg Ile Glu Ser Val Leu Ser Ser
                165                 170                 175

Ser Gly Lys Arg Leu Gly Cys Ile Lys Ile Ala Ala Ser Leu Lys Gly
            180                 185                 190

Ile

<210> SEQ ID NO 4
<211> LENGTH: 202
<212> TYPE: PRT
<213> ORGANISM: Artificial Sequence
<220> FEATURE:
<223> OTHER INFORMATION: GM2AP and one of the amino acids from position
      57 to 70 is glycosylated with (GlcNAc)2Fuc(Man)3
```

<400> SEQUENCE: 4

```
Met Gln Ser Leu Met Gln Ala Pro Leu Leu Ile Ala Leu Gly Leu Leu
1               5                   10                  15

Leu Ala Ala Pro Ala Gln Ala His Leu Lys Lys Pro Ser Gln Leu Ser
            20                  25                  30

Ser Phe Ser Trp Asp Asn Cys Asp Glu Gly Lys Asp Pro Ala Val Ile
        35                  40                  45

Arg Ser Leu Thr Leu Glu Pro Asp Pro Ile Ile Val Pro Gly Asn Val
50                  55                  60

Thr Leu Ser Val Met Gly Ser Thr Ser Val Pro Leu Ser Ser Pro Leu
65                  70                  75                  80

Lys Val Asp Leu Val Leu Glu Lys Glu Val Ala Gly Leu Trp Ile Lys
                85                  90                  95

Ile Pro Cys Thr Asp Tyr Ile Gly Ser Cys Thr Phe Glu His Phe Cys
            100                 105                 110

Asp Val Leu Asp Met Leu Ile Pro Thr Gly Glu Pro Cys Pro Glu Pro
        115                 120                 125

Leu Arg Thr Tyr Gly Leu Pro Cys His Cys Pro Phe Lys Glu Gly Thr
    130                 135                 140

Tyr Ser Leu Pro Lys Ser Glu Phe Val Val Pro Asp Leu Glu Leu Pro
145                 150                 155                 160

Ser Trp Leu Thr Thr Gly Asn Tyr Arg Ile Glu Ser Val Leu Ser Ser
                165                 170                 175

Ser Gly Lys Arg Leu Gly Cys Ile Lys Ile Ala Ala Ser Leu Lys Gly
            180                 185                 190

Ile Arg His His His His His His His His
        195                 200
```

<210> SEQ ID NO 5
<211> LENGTH: 113
<212> TYPE: PRT
<213> ORGANISM: Artificial Sequence
<220> FEATURE:
<223> OTHER INFORMATION: 21-2B5-F7 light chain variable region

<400> SEQUENCE: 5

```
Asp Ile Val Met Thr Gln Thr Ala Ser Ser Val Tyr Val Thr Pro Gly
1               5                   10                  15

Glu Ser Val Ser Ile Ser Cys Arg Ser Thr Lys Ser Leu Leu His Ser
            20                  25                  30

Asn Gly Asp Thr Tyr Leu Tyr Trp Phe Leu Gln Arg Pro Gly Gln Ser
        35                  40                  45

Pro Gln Leu Leu Ile Tyr Arg Met Ser Asn Leu Ala Pro Gly Val Pro
    50                  55                  60

Asp Arg Phe Ser Gly Gly Gly Ser Gly Thr Ala Phe Thr Leu Arg Ile
65                  70                  75                  80

Ser Arg Val Glu Ala Glu Asp Val Gly Val Tyr Tyr Leu Tyr Ala Thr
                85                  90                  95

Ser Thr Ile Ser Phe His Val Arg Cys Trp Asp Gln Ala Gly Ala Glu
            100                 105                 110

Thr
```

<210> SEQ ID NO 6
<211> LENGTH: 120
<212> TYPE: PRT

<213> ORGANISM: Artificial Sequence
<220> FEATURE:
<223> OTHER INFORMATION: 21-2B5-F7 heavy chain variable region

<400> SEQUENCE: 6

Glu Ile Gln Leu Gln Gln Ser Gly Ala Glu Leu Val Arg Pro Gly Thr
1               5                   10                  15

Ser Val Lys Ile Ser Cys Met Ala Ser Gly Tyr Ser Phe Thr Gly Tyr
            20                  25                  30

Asn Met Asn Trp Val Arg Gln Ser His Gly Arg Ser Leu Glu Trp Ile
        35                  40                  45

Gly Asn Ile Asn Pro Tyr Phe Gly Ser Pro Asn Tyr Asn Gln Lys Phe
50                  55                  60

Lys Gly Lys Ala Thr Leu Thr Leu Asp Arg Ser Ser Asn Thr Ala Tyr
65                  70                  75                  80

Met Gln Leu Asn Arg Val Thr Ser Glu Asp Ser Ala Val Tyr Tyr Cys
                85                  90                  95

Ala Ser Arg Gln Leu Gly Leu Gly Asp Thr Met Asp Tyr Trp Gly Gln
            100                 105                 110

Gly Thr Ser Val Thr Val Ser Ser
        115                 120

<210> SEQ ID NO 7
<211> LENGTH: 107
<212> TYPE: PRT
<213> ORGANISM: Artificial Sequence
<220> FEATURE:
<223> OTHER INFORMATION: 21-4E3-C8-A light chain variable region

<400> SEQUENCE: 7

Asp Ile Val Met Thr Gln Ser His Lys Phe Met Ser Thr Ser Val Gly
1               5                   10                  15

Asp Arg Val Thr Ile Thr Cys Lys Ala Ser Gln Asp Val Ser Thr Ala
            20                  25                  30

Val Gly Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Arg Phe Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ile Thr Pro Trp
                85                  90                  95

Thr Phe Gly Gly Gly Thr Lys Leu Glu Ile Lys
            100                 105

<210> SEQ ID NO 8
<211> LENGTH: 119
<212> TYPE: PRT
<213> ORGANISM: Artificial Sequence
<220> FEATURE:
<223> OTHER INFORMATION: 21-4E3-C8-A heavy chain variable region

<400> SEQUENCE: 8

Gln Val Gln Leu Gln Gln Pro Gly Ala Asp Phe Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

```
Gly Asn Ile Tyr Pro Gly Ser Gly Ser Thr Asn Tyr Asn Glu Lys Phe
            50                  55                  60

Lys Asn Lys Ala Thr Leu Thr Ile Asp Thr Ser Ser Thr Ala Tyr
 65                  70                  75                  80

Met Gln Leu Ser Ser Leu Thr Ser Asp Ser Ala Val Tyr Tyr Cys
                     85                  90                  95

Ser Arg Ser Thr Leu Tyr Ser Tyr Asp Asp Gly Ser Trp Gly Gln Gly
                100                 105                 110

Thr Thr Leu Thr Val Ser Ser
            115

<210> SEQ ID NO 9
<211> LENGTH: 107
<212> TYPE: PRT
<213> ORGANISM: Artificial Sequence
<220> FEATURE:
<223> OTHER INFORMATION: 21-4E3-C8-A heavy chain variable region

<400> SEQUENCE: 9

Asp Ile Gln Met Thr Gln Ser Pro Ser Ser Leu Ser Ala Ser Leu Gly
  1               5                  10                  15

Glu Arg Val Ser Leu Thr Cys Arg Ala Ser Gln Glu Ile Ser Gly Asp
                 20                  25                  30

Leu Ser Trp Leu Gln Gln Lys Pro Asp Gly Thr Ile Lys Arg Leu Ile
             35                  40                  45

Tyr Ala Ala Ser Thr Leu Ala Ser Gly Val Pro Lys Arg Phe Ser Gly
 50                  55                  60

Ser Arg Ser Gly Ser Asp Tyr Ser Leu Thr Ile Ser Gly Leu Glu Ser
 65                  70                  75                  80

Glu Asp Phe Ala Asp Tyr Tyr Cys Leu Gln Tyr Val Ser Tyr Pro Phe
                 85                  90                  95

Thr Phe Gly Ser Gly Thr Lys Leu Glu Ile Lys
                100                 105

<210> SEQ ID NO 10
<211> LENGTH: 117
<212> TYPE: PRT
<213> ORGANISM: Artificial Sequence
<220> FEATURE:
<223> OTHER INFORMATION: 21-4E3-C8-B heavy chain variable region

<400> SEQUENCE: 10

Gln Ile Gln Leu Gln Gln Ser Gly Pro Glu Leu Gly Lys Pro Gly Ala
  1               5                  10                  15

Ser Val Lys Ile Ser Cys Lys Ala Ser Asp Tyr Thr Phe Thr Asp Phe
                 20                  25                  30

Tyr Ile Ser Trp Val Lys Gln Arg Pro Gly Gln Gly Leu Glu Trp Ile
             35                  40                  45

Gly Trp Ile Tyr Pro Leu Asp Asp His Thr Lys Tyr Asn Glu Lys Phe
 50                  55                  60

Lys Gly Lys Ala Thr Leu Thr Val Asp Ile Ser Ser Asn Thr Val Tyr
 65                  70                  75                  80

Met Gln Leu Ser Ser Leu Thr Ser Glu Asp Ser Ala Val Tyr Phe Cys
                 85                  90                  95
```

```
Ala Arg Ile Tyr Gly Tyr Ala Met Asp Tyr Trp Gly Gln Gly Thr Ser
            100                 105                 110

Val Thr Val Ser Ser
        115

<210> SEQ ID NO 11
<211> LENGTH: 107
<212> TYPE: PRT
<213> ORGANISM: Artificial Sequence
<220> FEATURE:
<223> OTHER INFORMATION: 21-2H9-G2 light chain variable region

<400> SEQUENCE: 11

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Asp
            20                  25                  30

Leu Ser Trp Leu Gln Gln Lys Pro Asp Gly Thr Ile Lys Arg Leu Ile
        35                  40                  45

Tyr Ala Ala Ser Thr Leu Ala Ser Gly Val Pro Lys Arg Phe Ser Gly
    50                  55                  60

Ser Arg Ser Gly Thr Asp Tyr Ser Leu Thr Ile Ser Gly Leu Glu Ser
65                  70                  75                  80

Glu Asp Phe Ala Asp Tyr Tyr Cys Leu Gln Tyr Val Ser Tyr Pro Phe
                85                  90                  95

Thr Phe Gly Ser Gly Thr Lys Leu Glu Ile Lys
            100                 105

<210> SEQ ID NO 12
<211> LENGTH: 119
<212> TYPE: PRT
<213> ORGANISM: Artificial Sequence
<220> FEATURE:
<223> OTHER INFORMATION: 21-2H9-G2 heavy chain variable region

<400> SEQUENCE: 12

Gln Val Gln Leu Gln Gln Pro Gly Ala Asp Phe Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Gly Ser Gly Ser Thr Asn Tyr Asn Glu Lys Phe
    50                  55                  60

Lys Asn Lys Ala Thr Leu Thr Ile Asp Thr Ser Ser Ser Thr Ala Tyr
65                  70                  75                  80

Met Gln Leu Ser Ser Leu Thr Ser Asp Asp Ser Ala Val Tyr Tyr Cys
                85                  90                  95

Ser Arg Ser Thr Leu Tyr Ser Tyr Asp Asp Gly Ser Trp Gly Gln Gly
            100                 105                 110

Thr Thr Leu Thr Val Ser Ser
        115

<210> SEQ ID NO 13
<211> LENGTH: 107
<212> TYPE: PRT
<213> ORGANISM: Artificial Sequence
<220> FEATURE:
<223> OTHER INFORMATION: 21-4G4-B11 light chain variable region
```

<400> SEQUENCE: 13

Glu Ile Val Met Thr Gln Ser His Asn His Val His Ile Ser Gly Arg
1               5                   10                  15

Gln Gly His His His Leu Gln Gly Gln Ser Gly Cys Glu Tyr Cys Cys
                20                  25                  30

Arg Leu Val Ser Thr Glu Thr Arg Ala Ile Ser Ile Thr Thr Asp Phe
            35                  40                  45

Thr Gly His Pro Pro Gly Thr Leu Glu Ser Leu Ile Ala Phe Thr Gly
        50                  55                  60

Ser Arg Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ile Thr Pro Trp
                85                  90                  95

Thr Phe Gly Gly Gly Thr Lys Leu Glu Ile Lys
            100                 105

<210> SEQ ID NO 14
<211> LENGTH: 117
<212> TYPE: PRT
<213> ORGANISM: Artificial Sequence
<220> FEATURE:
<223> OTHER INFORMATION: 21-4G4-B11 heavy chain variable region

<400> SEQUENCE: 14

Gln Ile Gln Leu Gln Gln Ser Gly Pro Glu Leu Gly Lys Pro Gly Ala
1               5                   10                  15

Ser Val Lys Ile Ser Cys Lys Ala Ser Asp Tyr Thr Phe Thr Asp Phe
                20                  25                  30

Tyr Ile Ser Trp Val Lys Gln Arg Pro Gly Gln Gly Leu Glu Trp Ile
            35                  40                  45

Gly Trp Ile Tyr Pro Leu Asp Asp His Thr Lys Tyr Asn Glu Lys Phe
        50                  55                  60

Lys Gly Lys Ala Thr Leu Thr Val Asp Ile Ser Ser Asn Thr Val Tyr
65                  70                  75                  80

Met Gln Leu Ser Ser Leu Thr Ser Glu Asp Ser Ala Val Tyr Phe Cys
                85                  90                  95

Ala Arg Ile Tyr Gly Tyr Ala Met Asp Tyr Trp Gly Gln Gly Thr Ser
            100                 105                 110

Val Thr Val Ser Ser
        115

<210> SEQ ID NO 15
<211> LENGTH: 113
<212> TYPE: PRT
<213> ORGANISM: Artificial Sequence
<220> FEATURE:
<223> OTHER INFORMATION: 21-4B10-E1 light chain variable region

<400> SEQUENCE: 15

Asp Ile Val Met Thr Ser Glu Thr His Leu Cys Ile Cys His Ser Trp
1               5                   10                  15

Arg Val Ser Leu His Leu Leu Gln Val Tyr Ile Glu Ser Pro Ala Ile
                20                  25                  30

Ile Trp Arg His Leu Phe Val Leu Val Pro Thr Glu Ala Arg Pro Val
            35                  40                  45

Ser Ser Ala Pro Asp Ile Ser Asp Val Gln Pro Cys Pro Arg Ser Pro
        50                  55                  60

Thr Gln Val Gln Trp Arg Trp Val Arg Asn Cys Phe His Thr Glu Asn
65                  70                  75                  80

Gln Ile Ser Gly Gly Thr Gly Cys Gly Cys Leu Leu Leu Tyr Ala Thr
                85                  90                  95

Ser Thr Ile Ser Phe His Val Arg Cys Trp Asp Gln Ala Gly Ala Glu
            100                 105                 110

Thr

<210> SEQ ID NO 16
<211> LENGTH: 120
<212> TYPE: PRT
<213> ORGANISM: Artificial Sequence
<220> FEATURE:
<223> OTHER INFORMATION: 21-4B10-E1 heavy chain variable region

<400> SEQUENCE: 16

Glu Ile Gln Leu Gln Gln Ser Gly Ala Glu Leu Val Arg Pro Gly Thr
1               5                   10                  15

Ser Val Lys Ile Ser Cys Met Ala Ser Gly Tyr Ser Phe Thr Gly Tyr
                20                  25                  30

Asn Met Asn Trp Val Arg Gln Ser His Gly Arg Ser Leu Glu Trp Ile
            35                  40                  45

Gly Asn Ile Asn Pro Tyr Phe Gly Ser Pro Asn Tyr Asn Gln Lys Phe
50                  55                  60

Lys Gly Lys Ala Thr Leu Thr Leu Asp Arg Ser Ser Asn Thr Ala Tyr
65                  70                  75                  80

Met Gln Leu Asn Arg Val Thr Ser Glu Asp Ser Ala Val Tyr Tyr Cys
                85                  90                  95

Ala Ser Arg Gln Leu Gly Leu Gly Asp Thr Met Asp Tyr Trp Gly Gln
            100                 105                 110

Gly Thr Ser Val Thr Val Ser Ser
        115                 120

<210> SEQ ID NO 17
<211> LENGTH: 107
<212> TYPE: PRT
<213> ORGANISM: Artificial Sequence
<220> FEATURE:
<223> OTHER INFORMATION: 22-2E9-G12 light chain variable region

<400> SEQUENCE: 17

Asp Ile Val Met Thr Gln Ser Gln Lys Phe Met Ser Thr Ser Ile Gly
1               5                   10                  15

Asp Arg Val Ser Val Thr Cys Lys Ala Ser Gln Asn Val Asn Thr Asn
                20                  25                  30

Ile Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
50                  55                  60

Ser Gly Ser Gly Thr Asp Phe Thr Leu Thr Ile Ser Ser Val Gln Ser
65                  70                  75                  80

Glu Asp Leu Ala Glu Tyr Phe Cys Gln Gln Tyr Ile Gly Tyr Pro Tyr
                85                  90                  95

Thr Phe Gly Gly Gly Thr Lys Leu Glu Ile Lys
            100                 105

<210> SEQ ID NO 18

```
<211> LENGTH: 120
<212> TYPE: PRT
<213> ORGANISM: Artificial Sequence
<220> FEATURE:
<223> OTHER INFORMATION: 22-2E9-G12-A heavy chain variable region

<400> SEQUENCE: 18

Gln Val Gln Leu Gln Gln Pro Gly Ala Thr Leu Val Arg Pro Gly Ala
1               5                   10                  15

Ser Val Lys Leu Ser Cys Lys Ala Ser Gly Tyr Thr Phe Ile Asn Tyr
            20                  25                  30

Trp Ile Asn Trp Val Lys Trp Arg Pro Gly Gln Gly Leu Glu Trp Ile
        35                  40                  45

Gly Asn Ile Asn Pro Asn Cys Gly Val Thr Lys Tyr Asn Glu Gln Ile
    50                  55                  60

Lys Ser Glu Ala Thr Leu Thr Val Asp Lys Ser Ser Ile Ala Tyr
65                  70                  75                  80

Met Gln Leu Ser Ser Leu Thr Ser Glu Asp Ser Ala Val Tyr Tyr Cys
                85                  90                  95

Pro His Leu Leu Leu Arg Trp Leu Leu His Val Pro Phe Ala Met Val
            100                 105                 110

Tyr Trp Gly Gln Gly Thr Ser Val
        115                 120

<210> SEQ ID NO 19
<211> LENGTH: 118
<212> TYPE: PRT
<213> ORGANISM: Artificial Sequence
<220> FEATURE:
<223> OTHER INFORMATION: 22-2E9-G12-B heavy chain variable region

<400> SEQUENCE: 19

Glu Val Gln Leu Val Glu Thr Gly Gly Gly Leu Val Gln Pro Gln Gly
1               5                   10                  15

Ser Leu Lys Leu Ser Cys Ala Ala Ser Gly Phe Asn Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Thr Lys Ser Asn Ser Tyr Ala Thr Tyr Tyr Ala Asp
    50                  55                  60

Ser Val Lys Asp Arg Phe Ile Ile Ser Arg Asp Asp Ser Gln Ser Met
65                  70                  75                  80

Leu Tyr Leu Gln Met Asn Asn Leu Lys Thr Glu Asp Thr Ala Ile Phe
                85                  90                  95

Tyr Cys Val Val Thr Tyr Trp Gly Phe Ile Tyr Trp Gly Gln Gly Thr
            100                 105                 110

Leu Val Thr Val Ser Ala
        115

<210> SEQ ID NO 20
<211> LENGTH: 112
<212> TYPE: PRT
<213> ORGANISM: Artificial Sequence
<220> FEATURE:
<223> OTHER INFORMATION: 22-3E6-B11 light chain variable region

<400> SEQUENCE: 20

Asp Val Val Met Thr Gln Thr Pro Leu Thr Leu Ser Val Thr Ile Gly
1               5                   10                  15
```

```
Gln Pro Ala Ser Ile Ser Cys Lys Ser Ser Gln Ser Leu Leu Tyr Ser
            20                  25                  30

Asp Arg Lys Thr Tyr Leu Asn Trp Leu Phe Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Ile Tyr Tyr Cys Trp Gln Gly
                85                  90                  95

Thr His Phe Pro Gln Thr Phe Gly Gly Gly Thr Lys Leu Glu Ile Lys
            100                 105                 110
```

<210> SEQ ID NO 21
<211> LENGTH: 115
<212> TYPE: PRT
<213> ORGANISM: Artificial Sequence
<220> FEATURE:
<223> OTHER INFORMATION: 22-3E6-B11 heavy chain variable region

<400> SEQUENCE: 21

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ser Phe Thr Ala Tyr
            20                  25                  30

Tyr Ile His Trp Met Lys Gln Ser Pro Glu Lys Ser Leu Glu Trp Ile
        35                  40                  45

Gly Glu Ile Asn Pro Ser Thr Asp Asp Thr Thr Tyr Asn Gln Asn Phe
    50                  55                  60

Lys Ser Lys Ala Thr Leu Thr Val Asp Arg Ser Ser Arg Thr Ala Tyr
65                  70                  75                  80

Met Gln Leu Arg Ser Leu Thr Ser Glu Asp Ser Ala Val Tyr Phe Cys
                85                  90                  95

Ala Arg Tyr Gly Glu Gly Ala Tyr Trp Gly Gln Gly Thr Leu Val Thr
            100                 105                 110

Val Ser Ala
        115
```

<210> SEQ ID NO 22
<211> LENGTH: 112
<212> TYPE: PRT
<213> ORGANISM: Artificial Sequence
<220> FEATURE:
<223> OTHER INFORMATION: 22-4B11-B9 light chain variable region

<400> SEQUENCE: 22

```
Asp Val Val Met Thr Gln Ile Pro Leu Thr Leu Ser Val Ile Ile Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Ser
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95
```

Thr His Phe Pro Gln Thr Tyr Gly Gly Gly Thr Lys Leu Glu Ile Lys
               100                 105                 110

<210> SEQ ID NO 23
<211> LENGTH: 115
<212> TYPE: PRT
<213> ORGANISM: Artificial Sequence
<220> FEATURE:
<223> OTHER INFORMATION: 22-4B11-B9 heavy chain variable region

<400> SEQUENCE: 23

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Phe
                20                  25                  30

Pro His Ala Leu Gly Glu Ala Lys Ser Thr Lys Glu Pro Thr Val Asp
            35                  40                  45

Trp Arg Asp Ile Ser Ile Tyr Trp Trp Tyr Tyr Leu Gln Ser Glu Val
    50                  55                  60

Gln Gly Gln Gly His Ile Asp Cys Arg Gln Ile Leu Gln Tyr Ser Leu
65                  70                  75                  80

Tyr Ala Thr Gln Glu Pro Asp Ile Thr Arg Leu Cys Ser Leu Leu Leu
                85                  90                  95

Cys Lys Ile Arg Arg Gly Gly Leu Leu Gly Pro Arg Asp Ser Gly Leu
            100                 105                 110

Cys Leu Cys
        115

<210> SEQ ID NO 24
<211> LENGTH: 106
<212> TYPE: PRT
<213> ORGANISM: Artificial Sequence
<220> FEATURE:
<223> OTHER INFORMATION: 22-5B1-B2 light chain variable region

<400> SEQUENCE: 24

Ile Val Met Thr Gln Ser Pro Lys Ser Met Ser Met Ser Val Gly Glu
1               5                   10                  15

Arg Val Thr Leu Ser Cys Lys Ala Ser Glu Asn Val Gly Thr Tyr Val
                20                  25                  30

Ser Trp Tyr Gln Gln Lys Pro Glu Gln Ser Pro Lys Leu Leu Ile Tyr
            35                  40                  45

Gly Ala Ser Asn Arg Tyr Thr Gly Val Pro Asp Arg Phe Thr Gly Ser
    50                  55                  60

Gly Ser Ala Thr Asp Phe Thr Leu Thr Ile Ser Ser Val Gln Ala Glu
65                  70                  75                  80

Asp Leu Ala Asp Tyr His Cys Gly Gln Ser Tyr Ser Tyr Pro Leu Thr
                85                  90                  95

Phe Gly Ala Gly Thr Lys Leu Glu Leu Lys
            100                 105

<210> SEQ ID NO 25
<211> LENGTH: 115
<212> TYPE: PRT
<213> ORGANISM: Artificial Sequence
<220> FEATURE:
<223> OTHER INFORMATION: 22-5B1-B2 heavy chain variable region

<400> SEQUENCE: 25

Glu Val Gln Met Gln Gln Ser Gly Pro Glu Leu Val Lys Pro Gly Ala
1               5                   10                  15

Ser Val Glu Ile Ser Cys Lys Ala Ser Gly Tyr Ser Phe Thr Gly Tyr
            20                  25                  30

Tyr Ile His Trp Val Lys Gln Ser Pro Glu Lys Asn Leu Glu Trp Ile
        35                  40                  45

Gly Glu Val Asn Pro Ile Ser Gly Gly Thr Thr Tyr Asn Gln Arg Phe
50                  55                  60

Lys Ala Lys Ala Thr Leu Asn Val Asp Thr Leu Ser Asn Thr Ala Tyr
65                  70                  75                  80

Met Gln Leu Lys Ser Leu Thr Ser Glu Asp Ser Ala Val Tyr Phe Cys
                85                  90                  95

Ala Arg Tyr Gly Ala Thr Asp Tyr Trp Gly Gln Gly Thr Ser Val Thr
            100                 105                 110

Val Ser Ser
        115

<210> SEQ ID NO 26
<211> LENGTH: 115
<212> TYPE: PRT
<213> ORGANISM: Artificial Sequence
<220> FEATURE:
<223> OTHER INFORMATION: 22-5F2-E10 light chain variable region

<400> SEQUENCE: 26

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Ile His Trp Val Arg Arg Ser Pro Glu Lys Ser Leu Ala Trp Ile
        35                  40                  45

Gly Glu Ile Asn Pro Thr Thr Gly Gly Thr Ser Tyr Asn Gln Lys Phe
50                  55                  60

Arg Ala Lys Ala Thr Leu Thr Val Asp Thr Ser Ser Ser Thr Ala Tyr
65                  70                  75                  80

Ile Gln Leu Lys Ser Leu Thr Ser Glu Asp Ser Ala Ile Tyr Tyr Cys
                85                  90                  95

Ala Arg Tyr Gly Glu Gly Ala Tyr Trp Gly Gln Gly Thr Leu Val Thr
            100                 105                 110

Val Ser Ala
        115

<210> SEQ ID NO 27
<211> LENGTH: 113
<212> TYPE: PRT
<213> ORGANISM: Artificial Sequence
<220> FEATURE:
<223> OTHER INFORMATION: 22-5F2-E10 heavy chain variable region

<400> SEQUENCE: 27

Asp Val Val Leu Thr Gln Thr Pro Leu Thr Leu Ser Val Thr Phe Gly
1               5                   10                  15

Gln Pro Ala Ser Ile Ser Cys Lys Ser Ser Gln Ser Leu Phe Ile Ile
            20                  25                  30

Thr Trp Lys Asp Ile Phe Val Phe Gly Cys Tyr Arg Gly Gln Ala Ser
        35                  40                  45

Leu Gln Ser Ala Ile Ser Phe Trp Cys Leu Asn Trp Thr Leu Glu Ser
            50                  55                  60

Leu Thr Gly Ser Val Ala Val Asp Gln Gly Gln Ile Ser His Thr Arg
 65                  70                  75                  80

Ser Thr Glu Trp Arg Leu Arg Ile Trp Glu Phe Ile Ile Ala Gly Lys
                85                  90                  95

Val His Ile Phe Leu Arg Arg Thr Val Glu Ala Pro Cys Trp Lys Ser
            100                 105                 110

Asn

<210> SEQ ID NO 28
<211> LENGTH: 737
<212> TYPE: DNA
<213> ORGANISM: Artificial Sequence
<220> FEATURE:
<223> OTHER INFORMATION: 21-2B5-F7 light chain variable region

<400> SEQUENCE: 28
gttagatctg tgagcgagct gcgtagaatg agttcctggc gctgcttgtg ctctggatcc      60
ctggagccat tgggatatt gtgatgactc agactgcatc ctctgtatat gtcactcctg      120
gagagtcagt ctccatctcc tgcaggtcta ctaagagtct cctgcatagt aatggcgaca      180
cttatttgta ttggttccta cagaggccag gccagtctcc tcagctcctg atatatcgga      240
tgtccaacct tgccccagga gtccctgaca ggttcagtgg cggtgggtca ggaactgctt      300
tcacactgag aatcagtaga gtggaggctg aggatgtggg tgtttattac tgtatgcaa      360 catcttgaat atcctttcac gttcggtgct gggaccaagc tggagctgaa acgggctgat      420
gttgcaccaa ctgtatccat cttcccacca tccagtgagc agttaacatc tggaggtgcc      480
tcagtcgtgt gcttcttgaa caacttctac cccaaagaca tcaatgtcaa gtggaagatt      540
gatggcagtg aacgacaaaa tggcgtcctg aacagttgga ctgatcagga cagcaaagac      600
agcacctaca gcatgagcag caccctcacg ttgaccaagg acgagtatga acgacataac      660 agctataccl gtgaggccac tcacaagaca tcaacttcac cccattgtca agagcttcaa      720
caggatgagt gtacgcg                                                    737

<210> SEQ ID NO 29
<211> LENGTH: 730
<212> TYPE: DNA
<213> ORGANISM: Artificial Sequence
<220> FEATURE:
<223> OTHER INFORMATION: 21-2B5-F7 heavy chain variable region

<400> SEQUENCE: 29
tacaaagtaa ccactcaaag gataaaataa tcgcgaattt gccccccca agagacaacg      60 acgaagattg gggtcatcct cttccttctg tcagtaactg caggtgtcca ctctgagatc      120
cagctgcaac agtctggagc tgagctggtg aggcctggga cttcagtgaa gatatcctgc      180
atggcttctg gttactcatt cactggctac aatatgaact gggtgaggca aagccatgga      240
aggagccttg agtggatcgg aaatattaat ccttactttg gtagtcctaa ctacaatcag      300
aagttcaagg gcaaggccac attgacttta gacagatcct ccaacacagc ctacatgcaa      360
ctcaacagag tgacatctga ggactctgca gtctactact gtgcatcaag gcagctcggg      420
ctgggagata ctatggacta ctggggtcaa ggaacctcag tcaccgtctc ctcagccaaa      480
acaacagccc catcggtcta tccactggcc cctgtgtgtg gagatacaag tggctcctcg      540

```
gtgactctag gatgcctggt caagggttat ttccctgagc cagtgacctt gacctggaac      600
tctggatccc tgtccagtgg tgtgcacacc ttcccagctg tcctgcagtc tgacctctac      660
accctcagca gctcagtgac tgtaacctcg agcacctggc ccagccagtc catcacctgc      720
aattgtcgct                                                             730
```

```
<210> SEQ ID NO 30
<211> LENGTH: 651
<212> TYPE: DNA
<213> ORGANISM: Artificial Sequence
<220> FEATURE:
<223> OTHER INFORMATION: 21-4E3-C8-A light chain variable region

<400> SEQUENCE: 30
gtgtttctcc ggttgtctgg tgttgacgga gacattgtga tgacccagtc tcacaaattc       60
atgtccacat cagtgggaga cagggtcacc atcacctgca aggccagtca ggatgtgagt      120
actgctgtag ctggtatca acagaaacca gggcaatctc ctaaactact gatttactgg       180
gcatccaccc ggcacactgg agtccctgat cgcttcacag gcagtagatt tgggacagac      240
tatactctca ccatcagcag tgtgcaggct gaagacctgg cactttatta ctgtcagcaa      300
cattatatca ctccgtggac gttcggtgga ggcaccaagc tggaaatcaa acgggctgat      360
gctgcaccaa ctgtatccat cttcccacca tccagtgagc agttaacatc tggaggtgcc      420
tcagtcgtgt gcttcttgaa caacttctac cccaaagaca tcaatgtcaa gtggaagatt      480
gatggcagtg aacgacaaaa tggcgtcctg aacagttgga ctgatcagga cagcaaagac      540
agcacctaca gcatgagcag cacectcacg ttgaccaagg acgagtatga acgacataac      600
agctatacct gtgaggccac tcacaagacc acaacttcac ccattcaacg g              651
```

```
<210> SEQ ID NO 31
<211> LENGTH: 658
<212> TYPE: DNA
<213> ORGANISM: Artificial Sequence
<220> FEATURE:
<223> OTHER INFORMATION: 21-4E3-C8-A heavy chain variable region

<400> SEQUENCE: 31
cgacagtctt tttggttgca gcagctacag gtgtccactc ccaggtccaa ctgcagcagc       60
ctggtgctga cttttgtgaag cctgggggcct cagtgaagct gtcctgcaag gcttctggct     120
acactttcac cagctactgg ataaactggg tgaagcagag gcctggacaa ggccttgagt      180
ggattggaaa tatttatcct ggtagcggta gtactaacta caatgagaag ttcaagaaca      240
aggccacact gactatagac acatcctcca gcacagccta catgcagctc agcagcctga      300
catctgacga ctctgcggtc tactactgtt caagatcaac cctctatagt tacgacgacg      360
gctcttgggg ccaaggcacc actctcacag tctcctcagc caaaacgaca cccccatctg      420
tctatccact ggcccctgga tctgctgccc aaactaactc catggtgacc ctgggatgcc      480
tggtcaaggg ctatttccct gagccagtga cagtgacctg gaactctgga tccctgtcca      540
gcggtgtgca caccttccca gctgtcctgc agtctgacct ctacactctg agcagctcag      600
tgactgtccc ctccagcacc tggcccagcg agaccgtcac ctgcaacgtg cccctccc        658
```

```
<210> SEQ ID NO 32
<211> LENGTH: 653
<212> TYPE: DNA
<213> ORGANISM: Artificial Sequence
<220> FEATURE:
<223> OTHER INFORMATION: 21-4E3-C8-B light chain variable region
```

<400> SEQUENCE: 32

```
tgttgctctg gtttccaggt atcagatgtg acatccagat gacgcagtct ccatcctcct    60
tatctgcctc tctgggagaa agagtcagtc tcacttgtcg ggcaagtcag gaaattagtg   120
gtgacttaag ctggcttcag cagaaaccag atggaactat aaacgcctg atatacgccg    180
catccacttt agcttctggt gtcccaaaaa ggttcagtgg cagtaggtct gggtcagatt   240
attctctcac catcagcggc cttgagtctg aagattttgc agactattac tgtctacaat   300
atgttagtta ccattcacg ttcggctcgg ggacaaagtt ggaaataaaa cgggctgatg    360
ctgcaccaac tgtatccatc ttcccaccat ccagtgagca gttaacatct ggaggtgcct   420
cagtcgtgtg cttcttgaac aacttctacc ccaaagacat caatgtcaag tggaagattg   480
atggcagtga acgacaaaat ggcgtcctga acagttggac tgatcaggac agcaaagaca   540
gcacctacag catgagcagc accctcacgt tgaccaagga cgagtatgaa cgacataaca   600
gctataccctg tgaggccact tcacatagac agcaaatctc acccattcaa cag          653
```

<210> SEQ ID NO 33
<211> LENGTH: 653
<212> TYPE: DNA
<213> ORGANISM: Artificial Sequence
<220> FEATURE:
<223> OTHER INFORMATION: 21-4E3-C8-B heavy chain variable region

<400> SEQUENCE: 33

```
ttgaacttgc cattcctcct gtcaggaact gcaggtgtcc attgccagat ccagctgcag    60
cagtctggac ctgaactggg gaagcctggg gcttcagtga agatatcctg caaggcttct   120
gactacacct tcactgactt ctatataagt tgggtgaaac agaggcctgg acagggactt   180
gagtggattg gatggattta cctttagac gatcatacta gtacaatga aagttcaag     240
ggcaaggcca cattgactgt agacatatcc tccaacacag tctacatgca gctcagcagc   300
ctgacctctg aggactctgc ggtctatttc tgtgccagaa tctatggata tgctatggac   360
tactgggtc aaggaacctc agtcaccgtc tcctcagcca aaacaacagc ccatcggtc     420
tatccactag ccctgtgtg tggagataca actggctcct cggtgacttt aggatgcctg    480
gtcaagggtt atttccctga ccagtgacc ttgacctgga actctggatt cctgtccagt    540
ggtgtgcaca cctttccagc tgtcctgcag tctgacctct acaccctcag cagctcagcg   600
actgtaacct cgagcacctg gccagccat accataccg cagacggtcc ccc           653
```

<210> SEQ ID NO 34
<211> LENGTH: 751
<212> TYPE: DNA
<213> ORGANISM: Artificial Sequence
<220> FEATURE:
<223> OTHER INFORMATION: 21-2H9-G2 light chain variable region

<400> SEQUENCE: 34

```
gcggtcatct gcacgatcat gagggtacct cgctcacgtg ctttaagatt cttgtcagct    60
ctggttccca ggtatcagat gtgacatcca gatgacccag tctccatcct ccttatctgc   120
ctctctggga gaaagagtca gtctcacttg tcgggcaagt caggaaatta gtggtgactt   180
aagctggctt cagcagaaac cagatggaac tattaaacgc ctgatctacg ccgcatccac   240
tttagcttct ggtgtcccaa aaaggttcag tggcagtagg tctgggtgag attattctct   300
caccatcagc ggccttgagt ctgaagattt tgcagactat tactgtctac aatatgttag   360
```

```
ttatccattc acgttcggct cggggacaaa gttggaaata aaacgggctg atgctgcacc     420
aactgtatcc atcttcccac catccagtga gcagttaaca tctggaggtg cctcagtcgt     480
gtgcttcttg aacaacttct accccaaaga catcaatgtc aagtggaaga ttgatggcag     540
tgaacgacaa aatggcgtcc tgaacagttg gactgatcag dacagcaaag acagcaccta     600
cagcatgagc agcaccctca cgttgaccaa ggacgagtat gaacgacata cagctatac      660 ctgtgaggcc actcacaaga catcagtttt cccccattat cagagggctt tcaccaggaa     720
tgagtgtagc ccgccaaaaa aaaaaaaaaa c                                    751
```

<210> SEQ ID NO 35
<211> LENGTH: 660
<212> TYPE: DNA
<213> ORGANISM: Artificial Sequence
<220> FEATURE:
<223> OTHER INFORMATION: 21-2H9-G2 heavy chain variable region

<400> SEQUENCE: 35

```
cgtctgtctt tttggttgca gcagctacag gtgtccactc ccaggtccaa ctgcagcagc      60
ctggtgctga cttttgtgaag cctggggcct cagtgaagct gtcctgcaag gcttctggct    120
acactttcac cagctactgg ataaactggg tgaagcagag gcctggacaa ggccttgagt    180
ggattggaaa tatttatcct ggtagcggta gtactaacta caatgagaag ttcaagaaca    240
aggccacact gactatagac acatcctcca gcacagccta catgcagctc agcagcctga    300
catctgacga ctctgcggtc tactactgtt caagatcaac cctctatagt tacgacgacg    360
gctcttgggg ccaaggcacc actctcacag tctcctcagc caaaacgaca cccccatctg    420
tctatccact ggcccctgga tctgctgccc aaaactaac tccatggtga ccctgggatg    480
cctggtcaag ggctatttcc ctgagccagt gacagtgacc tggaactctg gatccctgtc    540
cagcggtgtg cacaccttcc cagctgtcct gcagtctgac ctctacactc tgagcagctc    600
agtgactgtc ccctccagca cctggcccag cgagaccgtc acctgcaacg tgcccgtcca    660
```

<210> SEQ ID NO 36
<211> LENGTH: 795
<212> TYPE: DNA
<213> ORGANISM: Artificial Sequence
<220> FEATURE:
<223> OTHER INFORMATION: 21-4G4-B11 light chain variable region

<400> SEQUENCE: 36

```
gactagagca cgtggtgtct ggtgttgacg gagaaattgt gatgacccag tctcacaatc      60
atgtccacat cagtgggaga cagggtcacc atcacctgca aggccagtca ggatgtgagt    120
actgctgtag gctggtatca acagaaacca gggcaatctc ctaaactact gattttactg    180
ggcatccacc cggcacactg gagtccctga tcgctttcac aggcagtaga tctgggacag    240
actatactct caccatcagc agtgtgcagg ctgaagacct ggcactttat tactgtcagc    300
aacattatat cactccgtgg acgttcggtg gaggcaccaa gctggaaatc aaacgggctg    360
atgctgcacc aactgtatcc atcttcccac catccagtga gcagttaaca tctggaggtg    420
cctcagtcgt gtgcttcttg aacaacttct accccaaaga catcaatgtc aagtggaaga    480
ttgatggcag tgaacgacaa aatggcgtcc tgaacagttg gactgatcag gacagcaaag    540
acagcaccta cagcatgagc agcaccctca cgttgaccaa ggacgagtat gaacgacata    600
acagctatac ctgtgaggcc actcacaaga catcaacttc acccattgtc aagagcttca    660
acaggaatga gtgtaggggg gggaaaaaa aaaaaaaaaa aaaaaaggcg gaggggacgc     720
```

```
ggataaaaat aaccgttagc atgacttaag tgcgtaacat attcaatctt tctttccgcg    780
ggggcgggaa agagg                                                     795

<210> SEQ ID NO 37
<211> LENGTH: 666
<212> TYPE: DNA
<213> ORGANISM: Artificial Sequence
<220> FEATURE:
<223> OTHER INFORMATION: 21-4G4-B11 heavy chain variable region

<400> SEQUENCE: 37
catgaatgga gctgggtcat tctcttcctc ctgtcaggaa ctgcaggtgt ccattgccag     60
atccagctgc agcagtctgg acctgaactg gggaagcctg ggcttcagt gaagatatcc    120 tgcaaggctt ctgactacac cttcactgac ttctatataa gttgggtgaa acagaggcct   180
ggacagggac ttgagtggat tggatggatt tatcctttag acgatcatac taagtacaat   240
gagaagttca aggcaaggc cacattgact gtagacatat cctccaacac agtctacatg    300
cagctcagca gcctgacctc tgaggactct gcggtctatt tctgtgccag aatctatgga   360
tatgctatgg actactgggg tcaaggaacc tcagtcaccg tctcctcagc caaaacaaca   420
gccccatcgg tctatccact ggcccctgtg tgtggagata caactggctc ctcggtgact   480
ctaggatgcc tggtcaaggg ttatttccct gagccagtga ccttgacctg aactctgga    540 tccctgtcca gtggtgtgca ccttcccag ctgtcctgc agtctgacct ctacaccctc     600
agcagctcag tgactgtaac ctcgagcacc tggcccagcc agtccatcac ctgcaatggc   660
ccgcag                                                              666

<210> SEQ ID NO 38
<211> LENGTH: 720
<212> TYPE: DNA
<213> ORGANISM: Artificial Sequence
<220> FEATURE:
<223> OTHER INFORMATION: 21-4B10-E1 light chain variable region

<400> SEQUENCE: 38 gcccccttt tttatggggg ggggaacttg cctcagctca gttccttggg ctgcttgtgc      60
tctggatccc tggagccatt ggggatattg tgatgacttc agaaactcac ctctgtatat   120
gtcactcctg gagagtcagt ctccatctcc tgcaggtcta ctaagagtct cctgcatagt   180
aatggcgaca cttatttgta ttggttccta cagaggccag gccagtctcc tcagctcctg   240
atatatcgga tgtccaacct tgccccagga gtccctgaca ggttcagtgg cggtgggtca   300
ggaactgctt tcacactgag aatcagtaga gtggaggctg aggatgtggg tgtttattac   360
tgtatgcaac atcttgaata tccttcacg ttcggtgctg gaccaagct ggagctgaaa     420 cgggctgatg ttgcaccaac tgtatccatc ttcccaccat ccagtgagca gttaacatct   480
ggaggtgcct cagtcgtgtg cttcttgaac aacttctacc ccaaagacat caatgtcaag   540
tggaagattg atggcagtga acgacaaaat ggcgtcctga cagttggac tgatcaggac    600 agcaaagaca gcacctacag catgagcagc accctcacgt tgaccaagga cgagtatgaa   660
cgacataaca gctaacctgt gaggccactc acaagacatc aacttcaccc attcaacggg   720

<210> SEQ ID NO 39
<211> LENGTH: 687
<212> TYPE: DNA
<213> ORGANISM: Artificial Sequence
<220> FEATURE:
```

<223> OTHER INFORMATION: 21-4B10-E1 heavy chain variable region

<400> SEQUENCE: 39

| agccttcccc cccccaaaggg aggggtgacc ttgctattcc ttctgtcagt aactgcaggt | 60 |
|---|---|
| gtccactctg agatccagct gcaacagtct ggagctgagc tggtgaggcc tgggacttca | 120 |
| gtgaagatat cctgcatggc ttctggttac tcattcactg ctacaatat gaactgggtg | 180 |
| aggcaaagcc atggaaggag ccttgagtgg atcggaaata ttaatcctta ctttggtagt | 240 |
| cctaactaca atcagaagtt caagggcaag gccacattga ctttagacag atcctccaac | 300 |
| acagcctaca tgcagctcaa cagagtgaca tctgaggact ctgcagtcta ctactgtgca | 360 |
| tcaaggcagc tcgggctggg agatactatg gactactggg gtcaaggaac ctcagtcacc | 420 |
| gtctcctcag ccaaaacaac agccccatcg gtctatccac tagcccctgt gtgtggagat | 480 |
| acaagtggct cctcggtgac tttaggatgc ctggtcaagg gttatttccc tgagccagtg | 540 |
| accttgacct ggaactctgg atccctgtcc agtggtgtgc acaccttccc agctgtcctg | 600 |
| cagtctgacc tctacaccct cagcagctca gtgactgtaa cctcgagcac ctggcccagc | 660 |
| tcagtccgtc gcactgcttg ctgttca | 687 |

<210> SEQ ID NO 40
<211> LENGTH: 680
<212> TYPE: DNA
<213> ORGANISM: Artificial Sequence
<220> FEATURE:
<223> OTHER INFORMATION: 22-2E9-G12 light chain variable region

<400> SEQUENCE: 40

| ggtcatactg ctgtggtgtc tggtgttgat ggagacattg tgatgaccca gtctcaaaaa | 60 |
|---|---|
| ttcatgtcca catcaatagg agacagggtc agcgtcacct gcaaggccag tcagaatgtg | 120 |
| aatactaata tagcctggta tcaacagaaa ccaggacagt ctcctaaagc actgatttac | 180 |
| tcggcttcct accgctatag tggagtccct gatcgcttca caggcagtgg atctgggaca | 240 |
| gatttcactc tcaccatcag cagtgtgcag tctgaggact tggcagaata tttctgtcag | 300 |
| caatatatcg gctatccgta cacgttcgga ggggggacca agctggaaat aaaacgggct | 360 |
| gatgctgcac caactgtatc catcttccca ccatccagtg agcagttaac atctggaggt | 420 |
| gcctcagtcg tgtgcttctt gaacaacttc taccccaaag acatcaatgt caagtggaag | 480 |
| attgatggca gtgaacgaca aaatggcgtc ctgaacagtt ggactgatca ggacagcaaa | 540 |
| gacagcacct acagcatgag cagcaccctc acgttgacca aggacgagta tgaacgacat | 600 |
| aacagctata cctgtgaggc cactcacaag acatcaactt cacccattgt caagagcttc | 660 |
| aacaggaatg agtgtaaccc | 680 |

<210> SEQ ID NO 41
<211> LENGTH: 676
<212> TYPE: DNA
<213> ORGANISM: Artificial Sequence
<220> FEATURE:
<223> OTHER INFORMATION: 22-2E9-G12-A heavy chain variable region

<400> SEQUENCE: 41

| gggtcatctc ttcttggtag caactgctac aggtgtccac tcccaggtcc aactgcagca | 60 |
|---|---|
| gcctggggct tgactggtga ggcctggggc ttcagtgaag ttgtcctgca aggcttctgg | 120 |
| ctacaccttc atcaactact ggataaactg ggtgaagtgg aggcctggac aaggccttga | 180 |
| gtggattgga aatattaatc ctaattgtgg tgttactaag tacaatgagc agatcaagag | 240 |

```
cgaggccaca ctgactgtag acaaatcctc cagcatagcc tacatgcaac tcagcagcct    300
gacatctgag gactctgcgg tctattactg tcctcattta ttactacgat ggttgctaca    360
cgtccccttt gctatggtct actggggtca aggaacctca gtcaccgtct cctcagccaa    420
aacaacagcc ccatcggtct atccactggc cctgtgtgt ggagatacaa gtggctcctc     480
ggtgactcta ggatgcctgg tcaagggtta tttccctgag ccagtgacct tgacctggaa    540
ctctggatcc ctgtccagtg gtgtgcacac cttcccagct gtcctgcagt ctgacctcta    600
caccctcagc agctcagtga ctgtaacctc gagcacctgg cccagccagt ccatcacctg    660
caattggccc tcccca                                                    676

<210> SEQ ID NO 42
<211> LENGTH: 726
<212> TYPE: DNA
<213> ORGANISM: Artificial Sequence
<220> FEATURE:
<223> OTHER INFORMATION: 22-2E9-G12-B heavy chain variable region

<400> SEQUENCE: 42
gtggggtcaa tatacattgt catgctgtta gggctgaagt gggttttctt tgttgttttt     60
tatcaaggtg tgcattgtga ggtgcagctt gttgagactg gtggaggatt ggtgcagcct    120
caagggtcat tgaaactctc atgtgcggcc tctggattca acttcaatac ctatgccatg    180
aactgggtcc gccaggctcc aggaaagggt ttggaatggg ttgctcgcat aagaactaaa    240
agtaattctt atgcaacata ttatgccgat tcagtgaaag acaggttcat catctccaga    300
gatgattccc aaagcatgct ctatctgcaa atgaacaact gaaaactga ggacacagcc     360 atattttact gtgtggttac ctactggggg tttatttact ggggccaagg gactctggtc    420
actgtctctg cagccaaaac aacagcccca tcggtctatc cactggcccc tgtgtgtgga    480
gatacaagtg gctcctcggt gactctagga tgcctggtca agggttattt ccctgagcca    540
gtgaccttga cctggaactc tggatccctg tccagtggtg tgcacacctt cccagctgtc    600
ctgcagtctg acctctacac cctcagcagc tcagtgactg taacctcgag cacctggccc    660
agccagtcca tcacctgcaa tgtggcccaa cacggcaagc agcacccgta aaaaaaaaa     720 tttggt                                                               726

<210> SEQ ID NO 43
<211> LENGTH: 788
<212> TYPE: DNA
<213> ORGANISM: Artificial Sequence
<220> FEATURE:
<223> OTHER INFORMATION: 22-3E6-B11 light chain variable region

<400> SEQUENCE: 43
agctcaacaa caaaaaaaac aaaaaacaaa aaagataaa atctacacgt gacgggagtt      60 gggggagag gcagtgctct tttttttagg ggggggggac actagttgcc tgttaggctg     120
ttggtgctct ggattcggga accaacggt gatgttgtga tgacccagac tccactcact     180
ttgtcggtta ccattggaca accagcctcc atatcttgca agtcaagtca gagcctctta    240
tatagtgata gaaagacata tttgaattgg ttgtttcaga ggccaggcca gtctccaaag    300
cgcctaatct atctggtctc taaactggac tctggagtcc ctgacaggtt cactggcagt    360
ggatcaggga cagatttcac actgaaaatc agcagagtgg aggctgagga tttgggaatt    420
tattattgct ggcaaggtac acattttcct cagacgttcg gtggaggcac caagttggaa    480
```

-continued

```
atcaaacggg ctgatgctgc accaactgta tccatcttcc caccatccag tgagcagtta     540
acatctggag gtgcctcagt cgtgtgcttc ttgaacaact tctaccccaa agacatcaaa     600
gtcaaagtgg aagattgatg gcagtgaacg acaaaatggc gtcctgaaca gttggactga     660
tcaggacagc aaagacagca cctacagcat gagcagcacc ctcacgttga ccaaggacga     720
gtatgaacga cataacagct atacctgtga ggccactcac aaagagatca aatttcaccc     780
attcaacg                                                              788
```

```
<210> SEQ ID NO 44
<211> LENGTH: 657
<212> TYPE: DNA
<213> ORGANISM: Artificial Sequence
<220> FEATURE:
<223> OTHER INFORMATION: 22-3E6-B11 heavy chain variable region

<400> SEQUENCE: 44
gtaggaagct gggttttcctc ttaatcctgt cagtaactac aggtgtccca ctctgaggtc      60
cagctgcagc agtctggacc tgagctggtg aagcctgggg cttcagtgaa gatgtcctgc     120
aaggcttctg gttactcatt cactgcctat acatacact ggatgaagca aagtcctgaa      180
aagagccttg agtggattgg agagattaat cctagcactg atgacacaac ctacaaccag     240
aacttcaagt ccaaggccac attgactgta gacaggtcct ccagaacagc ctacatgcaa     300
ctcaggagcc tgacatctga ggactctgca gtctatttct gtgcaagata cggcgagggg     360
gcttactggg gccaagggac tctggtcact gtctctgcag ccaaaacaac agccccatcg     420
gtctatccac tggcccctgt gtgtggagat acaagtggct cctcggtgac tctaggatgc     480
ctggtcaagg gttatttccc tgagccagtg accttgacct ggaactctgg atccctgtcc     540
agtggtgtgc acaccttccc agctgtcctg cagtctgacc tctacaccct cagcagctca     600
gtgactgtaa cctcgagcac ctggcccagc cagaccatca cctgcaatgt gctcgct       657
```

```
<210> SEQ ID NO 45
<211> LENGTH: 889
<212> TYPE: DNA
<213> ORGANISM: Artificial Sequence
<220> FEATURE:
<223> OTHER INFORMATION: 22-4B11-B9 light chain variable region

<400> SEQUENCE: 45
gcatcgcctt aacacgctcg tccttatttg ctacactgaa ggtgcccgta cgctttcggg      60
tatcgttgac atgaaatgcc cagtcatgcc gttggggtaa gcgttgacca ctgaagcttg     120
acagttaagc ctttgggtaa tcgttgaaca ataaaagatg ccagtttagc ctttggggct     180
tttatttata gggcgggaaa acactagtgc ctgttaggct gttggtgctc tggattcggg     240
aaaccaacgg tgatgttgtg atgacccaga ttccactcac tttgtcggtt atcattggac     300
aaccagcctc catctcttgc aagtcaagtc agagcctctt atatagtgat ggaaagacat     360
atttgaattg gttgttacag aggccaggcc agtctccaaa gcgcctaatc tatctggtgt     420
ctaaactgga ctctggagtc tctgacaggt tcactggcag tggatcaggg acagatttca     480
cactgaaaat cagcagagtg gaggctgagg atttgggagt ttattattgc tggcaaggta     540
cacattttcc gcagacgtac ggtggaggca ccaagctgga aatcaaacgg ctgatgctg      600 caccaactgt atccatcttc ccaccatcca gtgagcagtt aacatctgga ggtgcctcag     660
tcgtgtgctt cttgaacaac ttctacccca agacatcaa tgtcaagtgg aagattgatg     720
gcagtgaacg acaaaatggc gtcctgaaca gttggactga tcaggacagc aaagacagca     780
```

```
cctacagcat gagcagcacc ctcacgttga ccaaggacga gtatgaacga cataacagct      840
atacctggag gcccgcgtcg acacatcagc gccacctcag tgccaaggg                  889

<210> SEQ ID NO 46
<211> LENGTH: 757
<212> TYPE: DNA
<213> ORGANISM: Artificial Sequence
<220> FEATURE:
<223> OTHER INFORMATION: 22-4B11-B9 heavy chain variable region

<400> SEQUENCE: 46
acggtaatga agaaggggg tggacctggg tttttttttt gccgtttttt ttccaccttt       60
tttaaaattt ggggttaaaa ccccccccct ttttcaatgt agaacctggg ctttatttta     120
atcctgtcag taactacagg tgtccactct gaggtccagc tgcaacagtc tggacctgag     180
ctggtgaagc ctgggcgtc agtgaagatt cctgcaagg cttctggtta ctcattcact       240
ggttttcctc atgcactggg tgaagcaaag tcctgaaaag agccttgagt ggattggaga     300
gattaatcct agtactggtg gtactaccta caatcagagg ttcaaggcca aggccacatt     360
gactgtagac aaatcctaca gtacagccta tatgcaactc aggagcctga catctgaaga     420
ctctgcagtc tattactgtg caagatacgg cgaggggggct tactgggcc aagggactct    480 ggtctctgtc tctgcggcca aaacaacagc ccatcggtc tatccactgg cccctgtgtg     540
tggagataca agtggctcct cggtgactct aggatgcctg gtcagggtt atttccctga     600 gccagtgacc ttgacctgga actctggatc cctgtccagt ggtgtgcaca ccttcccagc    660
tgtcctgcag tctgacctct acaccctcag cagctcagtg actgtaacct cgagcacctg    720
gcccagccag tccatcacct gcatataatc ttgcaag                              757

<210> SEQ ID NO 47
<211> LENGTH: 1013
<212> TYPE: DNA
<213> ORGANISM: Artificial Sequence
<220> FEATURE:
<223> OTHER INFORMATION: 22-5B1-B2 light chain variable region

<400> SEQUENCE: 47
ctgttcatgc ctgcagacat gacagtcaga agatgagtta catcatcgag aatgaatagc      60
ttatgatatt cgattgttcg ataacaatgc atgacaaaca agctagtatg attgatccta     120
cggtcactca gatggttact atgcaagacg aaagaagaca gatgctacat atcaaactct     180
cttggtgcag gtcatttact tcctttttg atgagtactt tgcataaagt tcctagaggg      240
cagaccagct gttccatgat ttataaacct aggcccttct ccacggagat ctcaaaagca    300
tcataacttc actggggggg cccccctcaa atgtgggggg ggggaggac gccttatatc      360 cttgctgttc tggttatatg gtgctgatgg gaacattgta atgacccaat ctcccaaatc     420
catgtccatg tcagtaggag agagggtcac cttgagctgc aaggccagtg agaatgtggg    480
tacttatgta tcctggtatc aacagaaacc agagcagtct cctaaactgc tgatatacgg    540
ggcatccaac cggtacactg ggtcccccga tcgcttcaca ggcagtggat cagcaacaga    600
tttcactctg accatcagca gtgtgcaggc tgaagacctt gcagattatc actgtggaca    660
gagttacagc tatccgctca cgttcggtgc tgggaccaag ctggagctga acgggctga     720 tgctgcacca actgtatcca tcttcccacc atccagtgag cagttaacat ctggaggtgc    780
ctcagtcgtg tgcttcttga caacttctta cccccaaagac catcaaagtc aaagtggaag    840
```

| attgatggca gtgaacgaca aaatggcgtc ctgaacagtt ggactgatca ggacagcaaa | 900 |
| gacagcacct acagcatgag cagcaccctc acgttgacca aggacgagta tgaacgacat | 960 |
| aacagctata cctgtgaggc cactcacaag acatcaactt cacccattca agg | 1013 |

<210> SEQ ID NO 48
<211> LENGTH: 1066
<212> TYPE: DNA
<213> ORGANISM: Artificial Sequence
<220> FEATURE:
<223> OTHER INFORMATION: 22-5B1-B2 heavy chain variable region

<400> SEQUENCE: 48

| gtattatgtg aggtgtcttt tcctggtggc atcttcatcc tattgtcttc tgtcaacgtg | 60 |
| attttctttt atacagcttc tgtactcagt atttatatat tagtatgcat ttatttcttt | 120 |
| cttatctgtt ttcgtaatta cgtggggtta atcggactgt tagaaagctg tgttgagatt | 180 |
| tgctttttat gtttgcttta attaggatgc tattgatctg agtttgatat gtaattatac | 240 |
| agcatccatt tcgaatggta acagtaagct cttatgattt cgacaggat tcatgtacaa | 300 |
| aggttttagc aatggtgctt cctgggttct atgctggagt ctcttgttgt aattggtgga | 360 |
| agattttaa acattcgcta aaaagcagca agaataata agaaaaggt gttgaactgg | 420 |
| gtctttgttt taatcctgtc agtaactaca ggtgtccact ctgaggtcca gatgcagcag | 480 |
| tctggacctg agctggtgaa gcctgggct tcagtgaga tttcctgcaa ggcttctggt | 540 |
| tactcattca ctggctatta catacactgg gtgaagcaaa gtcctgaaaa gaaccttgaa | 600 |
| tggattggag aggttaatcc tattagtggt ggtactacct acaaccagag attcaaggcc | 660 |
| aaggccacat tgaatgtgga cacattatcc aacacagcct acatgcagct caagagcctg | 720 |
| acatctgagg actctgcagt ctatttctgt gcacgatacg gggctacgga ctattggggt | 780 |
| caaggaacct cagtcaccgt ctcctcagcc aaaacaacag ccccatcggt ctatccactg | 840 |
| gcccctgtgt gtggagatac aagtggctcc tcggtgactc taggatgcct ggtcaagggt | 900 |
| tatttccctg agccagtgac cttgacctgg aactctggat ccctgtccag tggtgtgcac | 960 |
| accttcccag ctgtcctgca gtctgacctc tacaccctca gcagctcagt gactgtaacc | 1020 |
| tcgagcacct ggcccagcca gtccatctac cgctatagaa cgtgca | 1066 |

<210> SEQ ID NO 49
<211> LENGTH: 767
<212> TYPE: DNA
<213> ORGANISM: Artificial Sequence
<220> FEATURE:
<223> OTHER INFORMATION: 22-5F2-E10 heavy chain variable region

<400> SEQUENCE: 49

| ttacaaaata aacagataag cgtttccatt aaacataaaa aatttatggt aacgcttttt | 60 |
| ttttttgggg gggggaacc aagttgcctg ttaggctgtt ggtgctctgg attcgggata | 120 |
| ccaacggtga tgttgtgctg acccagactc cactcacttt gtcggttacc tttgacaac | 180 |
| cagcctccat ctcttgcaag tcaagtcaga gcctctttat atagtgatgg aaagacatat | 240 |
| ttgtatttgg ttgttacaga ggccaggcca gtctccaaag cgcctaatct ttctggtgtc | 300 |
| taaactggac tctggagtcc ctgacaggtt cagtggcagt ggatcaggga cagatttcac | 360 |
| actgaagatc aacagagtgg aggctgagga tttgggaatt tattattgct ggcaaggtac | 420 |
| acattttcct cagacgtacg gtggaggcac catgctggaa atcaaacggg ctgatgctgc | 480 |
| accaactgta tccatcttcc caccatccag tgagcagtta acatctggag gtgcctcagt | 540 |

```
cgtgtgcttc ttgaacaact tctaccccaa agacatcaat gtcaagtgga agattgatgg      600
cagtgaacga caaaatggcg tcctgaacag ttggactgat caggacagca agacagcac      660 ctacagcatg agcagcaccc tcacgttgac caaggacgag tatgaacgac ataacagcta     720
tacctgtgag gtcactcaca agactatcaa cttcacccat tcaagtg                   767
```

```
<210> SEQ ID NO 50
<211> LENGTH: 737
<212> TYPE: DNA
<213> ORGANISM: Artificial Sequence
<220> FEATURE:
<223> OTHER INFORMATION: 22-5F2-E10 light chain variable region

<400> SEQUENCE: 50
acatacaatc aatcgaacat acacaaaaca ttaccctct tataaaacat ttcgttacac       60
ctccctactc ccccccgatg agtcgccggg ctttattta  aatcctgtca gtaactacag      120
gtgtccactc tgaggtccag ctgcagcagt ctggacctga actggtgaag cctgggcctt     180
cagtgaagat atcttgcaag gcttctggtt actcattcac tggctactac atacactggg    240
tgaggcgaag tcctgaaaag agccttgcgt ggattggaga gattaatcct accactggtg    300
gtacttccta aaccagaaa ttcagggcca aggccacatt gactgtagac acgtcgtcca     360
gcacagccta tattcagctc aagagcctga catctgagga ctctgcaatc tattactgtg    420
caagatacgg cgaggggggct tactggggcc aagggactct ggtcactgtc tctgcagcca   480
aaacaacagc cccatcggtc tatccactgg cccctgtgtg tggagataca agtgggctcc    540
ctcggtgact ctaggatgcc tggtcaaggg ttatttccct gagccagtga ccttgacctg    600
gaactctgga tccctgtcca gtggtgtgca caccttccca gctgtcctgc agtctgacct    660
ctacaccctc agcagctcag tgactgtaac ctcgagcacc tggcccagcc agtccatcac    720
ctcatacgac ctgctaa                                                    737
```

```
<210> SEQ ID NO 51
<211> LENGTH: 11
<212> TYPE: PRT
<213> ORGANISM: Artificial Sequence
<220> FEATURE:
<223> OTHER INFORMATION: 21-2B5-F7 LCDR1

<400> SEQUENCE: 51

Lys Ser Leu Leu His Ser Asn Gly Asp Thr Tyr
1               5                   10
```

```
<210> SEQ ID NO 52
<211> LENGTH: 3
<212> TYPE: PRT
<213> ORGANISM: Artificial Sequence
<220> FEATURE:
<223> OTHER INFORMATION: 21-2B5-F7 LCDR2

<400> SEQUENCE: 52

Arg Met Ser
1
```

```
<210> SEQ ID NO 53
<211> LENGTH: 9
<212> TYPE: PRT
<213> ORGANISM: Artificial Sequence
<220> FEATURE:
<223> OTHER INFORMATION: 21-2B5-F7 LCDR3
```

```
<400> SEQUENCE: 53

Tyr Ala Thr Ser Thr Ile Ser Phe His
1               5

<210> SEQ ID NO 54
<211> LENGTH: 8
<212> TYPE: PRT
<213> ORGANISM: Artificial Sequence
<220> FEATURE:
<223> OTHER INFORMATION: 21-2B5-F7 HCDR1

<400> SEQUENCE: 54

Gly Tyr Ser Phe Thr Gly Tyr Asn
1               5

<210> SEQ ID NO 55
<211> LENGTH: 8
<212> TYPE: PRT
<213> ORGANISM: Artificial Sequence
<220> FEATURE:
<223> OTHER INFORMATION: 21-2B5-F7 HCDR2

<400> SEQUENCE: 55

Ile Asn Pro Tyr Phe Gly Ser Pro
1               5

<210> SEQ ID NO 56
<211> LENGTH: 13
<212> TYPE: PRT
<213> ORGANISM: Artificial Sequence
<220> FEATURE:
<223> OTHER INFORMATION: 21-2B5-F7 HCDR3

<400> SEQUENCE: 56

Ala Ser Arg Gln Leu Gly Leu Gly Asp Thr Met Asp Tyr
1               5                   10

<210> SEQ ID NO 57
<211> LENGTH: 6
<212> TYPE: PRT
<213> ORGANISM: Artificial Sequence
<220> FEATURE:
<223> OTHER INFORMATION: 21-4E3-C8-A LCDR1

<400> SEQUENCE: 57

Gln Asp Val Ser Thr Ala
1               5

<210> SEQ ID NO 58
<211> LENGTH: 3
<212> TYPE: PRT
<213> ORGANISM: Artificial Sequence
<220> FEATURE:
<223> OTHER INFORMATION: 21-4E3-C8-A LCDR2

<400> SEQUENCE: 58

Trp Ala Ser
1

<210> SEQ ID NO 59
<211> LENGTH: 10
<212> TYPE: PRT
<213> ORGANISM: Artificial Sequence
<220> FEATURE:
<223> OTHER INFORMATION: 21-4E3-C8-A LCDR3
```

<400> SEQUENCE: 59

Gln Gln His Tyr Ile Thr Pro Trp Thr Phe
1               5                   10

<210> SEQ ID NO 60
<211> LENGTH: 8
<212> TYPE: PRT
<213> ORGANISM: Artificial Sequence
<220> FEATURE:
<223> OTHER INFORMATION: 21-4E3-C8-A HCDR1

<400> SEQUENCE: 60

Gly Tyr Thr Phe Thr Ser Tyr Trp
1               5

<210> SEQ ID NO 61
<211> LENGTH: 8
<212> TYPE: PRT
<213> ORGANISM: Artificial Sequence
<220> FEATURE:
<223> OTHER INFORMATION: 21-4E3-C8-A HCDR2

<400> SEQUENCE: 61

Ile Tyr Pro Gly Ser Gly Ser Thr
1               5

<210> SEQ ID NO 62
<211> LENGTH: 12
<212> TYPE: PRT
<213> ORGANISM: Artificial Sequence
<220> FEATURE:
<223> OTHER INFORMATION: 21-4E3-C8-A HCDR3

<400> SEQUENCE: 62

Ser Arg Ser Thr Leu Tyr Ser Tyr Asp Asp Gly Ser
1               5                   10

<210> SEQ ID NO 63
<211> LENGTH: 6
<212> TYPE: PRT
<213> ORGANISM: Artificial Sequence
<220> FEATURE:
<223> OTHER INFORMATION: 21-4E3-C8-B LCDR1

<400> SEQUENCE: 63

Gln Glu Ile Ser Gly Asp
1               5

<210> SEQ ID NO 64
<211> LENGTH: 3
<212> TYPE: PRT
<213> ORGANISM: Artificial Sequence
<220> FEATURE:
<223> OTHER INFORMATION: 21-4E3-C8-B LCDR2

<400> SEQUENCE: 64

Ala Ala Ser
1

<210> SEQ ID NO 65
<211> LENGTH: 9
<212> TYPE: PRT
<213> ORGANISM: Artificial Sequence
<220> FEATURE:
<223> OTHER INFORMATION: 21-4E3-C8-B LCDR3

```
<400> SEQUENCE: 65

Leu Gln Tyr Val Ser Tyr Pro Phe Thr
1               5

<210> SEQ ID NO 66
<211> LENGTH: 8
<212> TYPE: PRT
<213> ORGANISM: Artificial Sequence
<220> FEATURE:
<223> OTHER INFORMATION: 21-4E3-C8-B HCDR1

<400> SEQUENCE: 66

Asp Tyr Thr Phe Thr Asp Phe Tyr
1               5

<210> SEQ ID NO 67
<211> LENGTH: 8
<212> TYPE: PRT
<213> ORGANISM: Artificial Sequence
<220> FEATURE:
<223> OTHER INFORMATION: 21-4E3-C8-B HCDR2

<400> SEQUENCE: 67

Ile Tyr Pro Leu Asp Asp His Thr
1               5

<210> SEQ ID NO 68
<211> LENGTH: 10
<212> TYPE: PRT
<213> ORGANISM: Artificial Sequence
<220> FEATURE:
<223> OTHER INFORMATION: 21-4E3-C8-B HCDR3

<400> SEQUENCE: 68

Ala Arg Ile Tyr Gly Tyr Ala Met Asp Tyr
1               5                   10

<210> SEQ ID NO 69
<211> LENGTH: 6
<212> TYPE: PRT
<213> ORGANISM: Artificial Sequence
<220> FEATURE:
<223> OTHER INFORMATION: 21-2H9-G2 LCDR1

<400> SEQUENCE: 69

Gln Glu Ile Ser Gly Asp
1               5

<210> SEQ ID NO 70
<211> LENGTH: 3
<212> TYPE: PRT
<213> ORGANISM: Artificial Sequence
<220> FEATURE:
<223> OTHER INFORMATION: 21-2H9-G2 LCDR2

<400> SEQUENCE: 70

Ala Ala Ser
1

<210> SEQ ID NO 71
<211> LENGTH: 9
<212> TYPE: PRT
<213> ORGANISM: Artificial Sequence
<220> FEATURE:
<223> OTHER INFORMATION: 21-2H9-G2 LCDR3
```

<400> SEQUENCE: 71

Leu Gln Tyr Val Ser Tyr Pro Phe Thr
1               5

<210> SEQ ID NO 72
<211> LENGTH: 9
<212> TYPE: PRT
<213> ORGANISM: Artificial Sequence
<220> FEATURE:
<223> OTHER INFORMATION: 21-2H9-G2 HCDR1

<400> SEQUENCE: 72

Gly Tyr Thr Phe Thr Ser Tyr Trp Ile
1               5

<210> SEQ ID NO 73
<211> LENGTH: 8
<212> TYPE: PRT
<213> ORGANISM: Artificial Sequence
<220> FEATURE:
<223> OTHER INFORMATION: 21-2H9-G2 HCDR2

<400> SEQUENCE: 73

Ile Tyr Pro Gly Ser Gly Ser Thr
1               5

<210> SEQ ID NO 74
<211> LENGTH: 12
<212> TYPE: PRT
<213> ORGANISM: Artificial Sequence
<220> FEATURE:
<223> OTHER INFORMATION: 21-2H9-G2 HCDR3

<400> SEQUENCE: 74

Ser Arg Ser Thr Leu Tyr Ser Tyr Asp Asp Gly Ser
1               5                   10

<210> SEQ ID NO 75
<211> LENGTH: 6
<212> TYPE: PRT
<213> ORGANISM: Artificial Sequence
<220> FEATURE:
<223> OTHER INFORMATION: 21-4G4-B11 LCDR1

<400> SEQUENCE: 75

Ser Gly Cys Glu Tyr Cys
1               5

<210> SEQ ID NO 76
<211> LENGTH: 3
<212> TYPE: PRT
<213> ORGANISM: Artificial Sequence
<220> FEATURE:
<223> OTHER INFORMATION: 21-4G4-B11 LCDR2

<400> SEQUENCE: 76

Gly His Pro
1

<210> SEQ ID NO 77
<211> LENGTH: 9
<212> TYPE: PRT
<213> ORGANISM: Artificial Sequence
<220> FEATURE:
<223> OTHER INFORMATION: 21-4G4-B11 LCDR3

```
<400> SEQUENCE: 77

Gln Gln His Tyr Ile Thr Pro Trp Thr
1               5

<210> SEQ ID NO 78
<211> LENGTH: 8
<212> TYPE: PRT
<213> ORGANISM: Artificial Sequence
<220> FEATURE:
<223> OTHER INFORMATION: 21-4G4-B11 HCDR1

<400> SEQUENCE: 78

Asp Tyr Thr Phe Thr Asp Phe Tyr
1               5

<210> SEQ ID NO 79
<211> LENGTH: 8
<212> TYPE: PRT
<213> ORGANISM: Artificial Sequence
<220> FEATURE:
<223> OTHER INFORMATION: 21-4G4-B11 HCDR2

<400> SEQUENCE: 79

Ile Tyr Pro Leu Asp Asp His Thr
1               5

<210> SEQ ID NO 80
<211> LENGTH: 10
<212> TYPE: PRT
<213> ORGANISM: Artificial Sequence
<220> FEATURE:
<223> OTHER INFORMATION: 21-4G4-B11 HCDR3

<400> SEQUENCE: 80

Ala Arg Ile Tyr Gly Tyr Ala Met Asp Tyr
1               5                   10

<210> SEQ ID NO 81
<211> LENGTH: 11
<212> TYPE: PRT
<213> ORGANISM: Artificial Sequence
<220> FEATURE:
<223> OTHER INFORMATION: 21-4B10-E1 LCDR1

<400> SEQUENCE: 81

Ile Glu Ser Pro Ala Ile Ile Trp Arg His Leu
1               5                   10

<210> SEQ ID NO 82
<211> LENGTH: 3
<212> TYPE: PRT
<213> ORGANISM: Artificial Sequence
<220> FEATURE:
<223> OTHER INFORMATION: 21-4B10-E1 LCDR2

<400> SEQUENCE: 82

Ser Asp Val
1

<210> SEQ ID NO 83
<211> LENGTH: 9
<212> TYPE: PRT
<213> ORGANISM: Artificial Sequence
<220> FEATURE:
<223> OTHER INFORMATION: 21-4B10-E1 LCDR3
```

```
<400> SEQUENCE: 83

Tyr Ala Thr Ser Thr Ile Ser Phe His
1               5

<210> SEQ ID NO 84
<211> LENGTH: 8
<212> TYPE: PRT
<213> ORGANISM: Artificial Sequence
<220> FEATURE:
<223> OTHER INFORMATION: 21-4B10-E1 HCDR1

<400> SEQUENCE: 84

Gly Tyr Ser Phe Thr Gly Tyr Asn
1               5

<210> SEQ ID NO 85
<211> LENGTH: 8
<212> TYPE: PRT
<213> ORGANISM: Artificial Sequence
<220> FEATURE:
<223> OTHER INFORMATION: 21-4B10-E1 HCDR2

<400> SEQUENCE: 85

Ile Asn Pro Tyr Phe Gly Ser Pro
1               5

<210> SEQ ID NO 86
<211> LENGTH: 13
<212> TYPE: PRT
<213> ORGANISM: Artificial Sequence
<220> FEATURE:
<223> OTHER INFORMATION: 21-4B10-E1 HCDR3

<400> SEQUENCE: 86

Ala Ser Arg Gln Leu Gly Leu Gly Asp Thr Met Asp Tyr
1               5                   10

<210> SEQ ID NO 87
<211> LENGTH: 6
<212> TYPE: PRT
<213> ORGANISM: Artificial Sequence
<220> FEATURE:
<223> OTHER INFORMATION: 22-2E9-G12 LCDR1

<400> SEQUENCE: 87

Gln Asn Val Asn Thr Asn
1               5

<210> SEQ ID NO 88
<211> LENGTH: 3
<212> TYPE: PRT
<213> ORGANISM: Artificial Sequence
<220> FEATURE:
<223> OTHER INFORMATION: 22-2E9-G12 LCDR2

<400> SEQUENCE: 88

Ser Ala Ser
1

<210> SEQ ID NO 89
<211> LENGTH: 9
<212> TYPE: PRT
<213> ORGANISM: Artificial Sequence
<220> FEATURE:
<223> OTHER INFORMATION: 22-2E9-G12 LCDR3
```

<400> SEQUENCE: 89

Gln Gln Tyr Ile Gly Tyr Pro Tyr Thr
1               5

<210> SEQ ID NO 90
<211> LENGTH: 8
<212> TYPE: PRT
<213> ORGANISM: Artificial Sequence
<220> FEATURE:
<223> OTHER INFORMATION: 22-2E9-G12-A HCDR1

<400> SEQUENCE: 90

Gly Tyr Thr Phe Ile Asn Tyr Trp
1               5

<210> SEQ ID NO 91
<211> LENGTH: 7
<212> TYPE: PRT
<213> ORGANISM: Artificial Sequence
<220> FEATURE:
<223> OTHER INFORMATION: 22-2E9-G12-A HCDR2

<400> SEQUENCE: 91

Ile Asn Pro Asn Cys Gly Val
1               5

<210> SEQ ID NO 92
<211> LENGTH: 17
<212> TYPE: PRT
<213> ORGANISM: Artificial Sequence
<220> FEATURE:
<223> OTHER INFORMATION: 22-2E9-G12-A HCDR3

<400> SEQUENCE: 92

Pro His Leu Leu Leu Arg Trp Leu Leu His Val Pro Phe Ala Met Val
1               5                   10                  15

Tyr

<210> SEQ ID NO 93
<211> LENGTH: 8
<212> TYPE: PRT
<213> ORGANISM: Artificial Sequence
<220> FEATURE:
<223> OTHER INFORMATION: 22-2E9-G12-B HCDR1

<400> SEQUENCE: 93

Gly Phe Asn Phe Asn Thr Tyr Ala
1               5

<210> SEQ ID NO 94
<211> LENGTH: 10
<212> TYPE: PRT
<213> ORGANISM: Artificial Sequence
<220> FEATURE:
<223> OTHER INFORMATION: 22-2E9-G12-B HCDR2

<400> SEQUENCE: 94

Ile Arg Thr Lys Ser Asn Ser Tyr Ala Thr
1               5                   10

<210> SEQ ID NO 95
<211> LENGTH: 9
<212> TYPE: PRT
<213> ORGANISM: Artificial Sequence
<220> FEATURE:
<223> OTHER INFORMATION: 22-2E9-G12-B HCDR3

```
<400> SEQUENCE: 95

Val Val Thr Tyr Trp Gly Phe Ile Tyr
1               5

<210> SEQ ID NO 96
<211> LENGTH: 11
<212> TYPE: PRT
<213> ORGANISM: Artificial Sequence
<220> FEATURE:
<223> OTHER INFORMATION: 22-3E6-B11 LCDR1

<400> SEQUENCE: 96

Gln Ser Leu Leu Tyr Ser Asp Arg Lys Thr Tyr
1               5                   10

<210> SEQ ID NO 97
<211> LENGTH: 3
<212> TYPE: PRT
<213> ORGANISM: Artificial Sequence
<220> FEATURE:
<223> OTHER INFORMATION: 22-3E6-B11 LCDR2

<400> SEQUENCE: 97

Leu Val Ser
1

<210> SEQ ID NO 98
<211> LENGTH: 9
<212> TYPE: PRT
<213> ORGANISM: Artificial Sequence
<220> FEATURE:
<223> OTHER INFORMATION: 22-3E6-B11 LCDR3

<400> SEQUENCE: 98

Trp Gln Gly Thr His Phe Pro Gln Thr
1               5

<210> SEQ ID NO 99
<211> LENGTH: 8
<212> TYPE: PRT
<213> ORGANISM: Artificial Sequence
<220> FEATURE:
<223> OTHER INFORMATION: 22-3E6-B11 HCDR1

<400> SEQUENCE: 99

Gly Tyr Ser Phe Thr Ala Tyr Tyr
1               5

<210> SEQ ID NO 100
<211> LENGTH: 8
<212> TYPE: PRT
<213> ORGANISM: Artificial Sequence
<220> FEATURE:
<223> OTHER INFORMATION: 22-3E6-B11 HCDR2

<400> SEQUENCE: 100

Ile Asn Pro Ser Thr Asp Asp Thr
1               5

<210> SEQ ID NO 101
<211> LENGTH: 8
<212> TYPE: PRT
<213> ORGANISM: Artificial Sequence
<220> FEATURE:
<223> OTHER INFORMATION: 22-3E6-B11 HCDR3
```

```
<400> SEQUENCE: 101

Ala Arg Tyr Gly Glu Gly Ala Tyr
1               5

<210> SEQ ID NO 102
<211> LENGTH: 11
<212> TYPE: PRT
<213> ORGANISM: Artificial Sequence
<220> FEATURE:
<223> OTHER INFORMATION: 22-4B11-B9 LCDR1

<400> SEQUENCE: 102

Gln Ser Leu Leu Tyr Ser Asp Gly Lys Thr Tyr
1               5                   10

<210> SEQ ID NO 103
<211> LENGTH: 3
<212> TYPE: PRT
<213> ORGANISM: Artificial Sequence
<220> FEATURE:
<223> OTHER INFORMATION: 22-4B11-B9 LCDR2

<400> SEQUENCE: 103

Leu Val Ser
1

<210> SEQ ID NO 104
<211> LENGTH: 9
<212> TYPE: PRT
<213> ORGANISM: Artificial Sequence
<220> FEATURE:
<223> OTHER INFORMATION: 22-4B11-B9 LCDR3

<400> SEQUENCE: 104

Trp Gln Gly Thr His Phe Pro Gln Thr
1               5

<210> SEQ ID NO 105
<211> LENGTH: 8
<212> TYPE: PRT
<213> ORGANISM: Artificial Sequence
<220> FEATURE:
<223> OTHER INFORMATION: 22-4B11-B9 HCDR1

<400> SEQUENCE: 105

Gly Tyr Ser Phe Thr Gly Phe Pro
1               5

<210> SEQ ID NO 106
<211> LENGTH: 7
<212> TYPE: PRT
<213> ORGANISM: Artificial Sequence
<220> FEATURE:
<223> OTHER INFORMATION: 22-4B11-B9 HCDR2

<400> SEQUENCE: 106

Ile Ser Ile Tyr Trp Trp Tyr
1               5

<210> SEQ ID NO 107
<211> LENGTH: 8
<212> TYPE: PRT
<213> ORGANISM: Artificial Sequence
<220> FEATURE:
<223> OTHER INFORMATION: 22-4B11-B9 HCDR3
```

```
<400> SEQUENCE: 107

Cys Lys Ile Arg Arg Gly Gly Leu
1               5

<210> SEQ ID NO 108
<211> LENGTH: 6
<212> TYPE: PRT
<213> ORGANISM: Artificial Sequence
<220> FEATURE:
<223> OTHER INFORMATION: 22-5B1-B2 LCDR1

<400> SEQUENCE: 108

Glu Asn Val Gly Thr Tyr
1               5

<210> SEQ ID NO 109
<211> LENGTH: 3
<212> TYPE: PRT
<213> ORGANISM: Artificial Sequence
<220> FEATURE:
<223> OTHER INFORMATION: 22-5B1-B2 LCDR2

<400> SEQUENCE: 109

Gly Ala Ser
1

<210> SEQ ID NO 110
<211> LENGTH: 9
<212> TYPE: PRT
<213> ORGANISM: Artificial Sequence
<220> FEATURE:
<223> OTHER INFORMATION: 22-5B1-B2 LCDR3

<400> SEQUENCE: 110

Gly Gln Ser Tyr Ser Tyr Pro Leu Thr
1               5

<210> SEQ ID NO 111
<211> LENGTH: 8
<212> TYPE: PRT
<213> ORGANISM: Artificial Sequence
<220> FEATURE:
<223> OTHER INFORMATION: 22-5B1-B2 HCDR1

<400> SEQUENCE: 111

Gly Tyr Ser Phe Thr Gly Tyr Tyr
1               5

<210> SEQ ID NO 112
<211> LENGTH: 8
<212> TYPE: PRT
<213> ORGANISM: Artificial Sequence
<220> FEATURE:
<223> OTHER INFORMATION: 22-5B1-B2 HCDR2

<400> SEQUENCE: 112

Val Asn Pro Ile Ser Gly Gly Thr
1               5

<210> SEQ ID NO 113
<211> LENGTH: 8
<212> TYPE: PRT
<213> ORGANISM: Artificial Sequence
<220> FEATURE:
<223> OTHER INFORMATION: 22-5B1-B2 HCDR3
```

```
<400> SEQUENCE: 113

Ala Arg Tyr Gly Ala Thr Asp Tyr
1               5

<210> SEQ ID NO 114
<211> LENGTH: 8
<212> TYPE: PRT
<213> ORGANISM: Artificial Sequence
<220> FEATURE:
<223> OTHER INFORMATION: 22-5F2-E10 LCDR1

<400> SEQUENCE: 114

Gly Tyr Ser Phe Thr Gly Tyr Tyr
1               5

<210> SEQ ID NO 115
<211> LENGTH: 8
<212> TYPE: PRT
<213> ORGANISM: Artificial Sequence
<220> FEATURE:
<223> OTHER INFORMATION: 22-5F2-E10 LCDR2

<400> SEQUENCE: 115

Ile Asn Pro Thr Thr Gly Gly Thr
1               5

<210> SEQ ID NO 116
<211> LENGTH: 8
<212> TYPE: PRT
<213> ORGANISM: Artificial Sequence
<220> FEATURE:
<223> OTHER INFORMATION: 22-5F2-E10 LCDR3

<400> SEQUENCE: 116

Ala Arg Tyr Gly Glu Gly Ala Tyr
1               5

<210> SEQ ID NO 117
<211> LENGTH: 11
<212> TYPE: PRT
<213> ORGANISM: Artificial Sequence
<220> FEATURE:
<223> OTHER INFORMATION: 22-5F2-E10 HCDR1

<400> SEQUENCE: 117

Gln Ser Leu Phe Ile Ile Thr Trp Lys Asp Ile
1               5                   10

<210> SEQ ID NO 118
<211> LENGTH: 3
<212> TYPE: PRT
<213> ORGANISM: Artificial Sequence
<220> FEATURE:
<223> OTHER INFORMATION: 22-5F2-E10 HCDR2

<400> SEQUENCE: 118

Trp Cys Leu
1

<210> SEQ ID NO 119
<211> LENGTH: 8
<212> TYPE: PRT
<213> ORGANISM: Artificial Sequence
<220> FEATURE:
<223> OTHER INFORMATION: 22-5F2-E10 HCDR3
```

-continued

```
<400> SEQUENCE: 119

Gly Lys Val His Ile Phe Leu Arg
1               5
```

ANTI-GM2AP ANTIBODY AND APPLICATIONS THEREOF

FIELD OF INVENTION

This present disclosure relates to a novel recombinant antibody or any antigen-binding fragments thereof. Specifically, the present disclosure relates to a novel recombinant antibody or any antigen-binding fragments thereof against GM2-activator protein (GM2AP) and their applications.

Sequence Listing

This application contains a sequence listing which has been submitted in ASCII text format via EFS-Web and is hereby incorporated by reference in its entirety. The .txt file contains a sequence listing, created on Oct. 29, 2021, is named 109283USI-SEQLIST-20211029_ST25.txt and is 70,253 bytes in size.

BACKGROUND OF THE INVENTION

GM2-activator protein (GM2AP) is a small monomeric protein containing a single site for Asn linked glycosylation. It is first synthesized as a precursor which is then glycosylated, modified and cleaved at $^{32}$Ser to be in the mature form. Mature GM2AP is a glycoprotein with molecular mass of 17.6 kDa in its deglycosylated form. Acting as a cofactor, GM2AP contains at least three functional features including a hydrophobic pocket called the β-cup structure, an oligosaccharide binding site, and an area that interacts with Hex A. The area that interacts with Hex A contributes to the degradation of GM2 ganglioside to GM3 by lysosomal β-hexminidase A (Hex A). However, only one-third of the synthesized of GM2AP is secreted. Cells can recapture the GM2AP via a carbohydrate-independent mechanism by various cells such as epidermal keratinocytes and fibroblast cells. A lack of the functional GM2AP is a cause of the abnormal accumulation of GM2 ganglioside in tissues of patients with the AB variant of GM2 gangliosidosis disease (a severe lysosomal storage disorder). The inherited deficiency of GM2AP was also related to the changing level of ganglioside and tumor associated gangliosides involving in cancer progression. Tumor-associated gangliosides are a result of initial oncogenic transformation and play a role in the induction of invasion and metastasis. Tumor cells synthesized and shed gangliosides into their microenvironments, and this leads to elevated levels of tumor-associated gangliosides in the serum. Moreover, gangliosides are known to exhibit regulatory roles in cell growth, adhesion, cell-cell interactions and signal transduction.

SUMMARY OF THE INVENTION

In view of the urgent need of the art, provided herein are embodiments illustrated hereinafter.

In one embodiment, the present application provides a recombinant antibody or the antigen-binding fragment thereof which specifically binds GM2-activator protein (GM2AP), wherein the recombinant antibody or the antigen-binding fragment thereof comprises (a) a light chain variable region (LCVR) comprising three light chain complementary determining regions (LCDR1-3) amino acid sequences which are independently selected from the group consisting of SEQ ID NOs: 51-53, 57-59, 63-65, 69-71, 75-77, 81-83, 87-89, 96-98, 102-104, 108-110 and 114-116; and (b) a heavy chain variable region (HCVR) comprising three heavy chain complementary determining regions (HCDR1-3) amino acid sequences which are independently selected from the group consisting of SEQ ID NOs: 54-56, 60-62, 66-68, 72-74, 78-80, 84-86, 90-92, 93-95, 99-101, 105-107, 111-113, and 117-119.

Preferably, the LCVR comprises an amino acid sequence which is selected from the group consisting of SEQ ID NOs: 5, 7, 9, 11, 13, 15, 17, 20, 22, 24 and 26, and/or the HCVR comprises an amino acid sequence which is selected from the group consisting of SEQ ID NOs: 6, 8, 10, 12, 14, 16, 18, 19, 21, 23, 25 and 27.

More preferably, the LCVR/HCVR pair comprises the amino acid sequence pairs of SEQ ID NOs: 5/6, 7/8, 9/10, 11/12, 13/14, 15/16, 17/18, 17/19, 20/21; 22/23, 24/25 or 26/27, respectively.

Preferably, the LCDR1/LCDR2/LCDR3 has an amino acid sequence of SEQ ID NOs: 51/52/53, 57/58/59, 63/64/65, 69/70/71, 75/76/77, 81/82/83, 87/88/89, 96/97/98, 102/103/104, 108/109/110 or 114/115/116, respectively.

Preferably, the HCDR1/HCDR2/HCDR3 has an amino acid sequence of SEQ ID NOs: 54/55/56, 60/61/62, 66/67/68, 72/73/74, 78/79/80, 84/85/86, 90/91/92, 93/94/95, 99/100/101, 105/106/107, 111/112/113 or 117/118/119, respectively.

More preferably, the LCDR1/LCDR2/LCDR3/HCDR1/HCDR2/HCDR3 have amino acid sequences of SEQ ID NOs: 51/52/53/54/55/56, 57/58/59/60/61/62, 63/64/65/66/67/68, 69/70/71/72/73/74, 75/76/77/78/79/80, 81/82/83/84/85/86, 87/88/89/90/91/92, 87/88/89/93/94/95, 96/97/98/99/100/101, 102/103/104/105/106/107, 108/109/110/111/112/113, or 114/115/116/117/118/119, respectively.

In any one of the foregoing embodiments, the recombinant antibody or the antigen-binding fragment thereof is selected from the group consisting of a diabody, a Fab, a Fab', a F(ab')$_2$, an Fv fragment, a disulfide stabilized Fv fragment (dsFv), a (dsFv)$_2$, a bispecific dsFv (dsfv-dsfv'), a disulfide stabilized diabody (ds diabody), a single-chain antibody molecule (scfv), an scfv dimer (bivalent diabody) and any combination thereof.

In any one of the foregoing embodiments, the recombinant antibody or the antigen-binding fragment thereof is selected from the group consisting of a monoclonal antibody, multispecific antibody, human antibody, humanized antibody, chimeric antibody and any combination thereof.

In any one of the foregoing embodiments, the recombinant antibody or the antigen-binding fragment thereof is a human antibody.

In one embedment, the present application provides a polynucleotide encoding any one of the recombinant antibodies or the antigen-binding fragments thereof mentioned in the present disclosure. The polynucleotide comprises a nucleic acid sequence which is selected from the group consisting of SEQ ID NOs: 28-50.

Preferably, the nucleic acid sequence encoding the LCVR is selected from the group consisting of SEQ ID NOs: 28, 30, 32, 34, 36, 38, 40, 43, 45, 47 and 50, and/or the nucleic acid sequence encoding the HCVR is selected from the group consisting of SEQ ID NOs: 29, 31, 33, 35, 37, 39, 41, 42, 44, 46, 48 and 49.

In any one of the foregoing embodiments, the LCVR/HCVR is encoded by the nucleic acid sequence pair of SEQ ID NOs: 28/29, 30/31, 32/33, 34/35, 36/37, 38/39, 40/41, 40/42, 43/44, 45/46, 47/48, or 50/49, respectively.

In one embedment, the present application provides a vector comprising any one of the polynucleotides mentioned in the present disclosure.

In one embodiment, the present application provides a host cell comprising the vector mentioned in the present disclosure.

Preferably, the host cell is selected from the group consisting of Chinese Hamster Ovary (CHO) cell, NSO cell, BHK cell, SP2/0 cell, HEK 293 cell, HEK 293 EBNA cell, PER.C6 cell, COS cell, 239F cell, SF9 cell, SF21 cell and a combination thereof.

In one embodiment, the present application provides a kit for detecting a GM2-activator protein (GM2AP) in a biological sample, wherein the kit comprises the recombinant antibody or the antigen-binding fragment thereof mentioned in the present disclosure.

Preferably, the kit further comprises a substrate, and a second antibody which conjugates with a signal generating unit and binds to a Fc domain of the recombinant antibody or the antigen-binding fragment thereof. The substrate is configured to react with the signal generating unit to generate a signal.

In any one of the foregoing embodiments, the biological sample comprises whole blood, serum, plasma, urine, or a combination thereof.

In any one of the foregoing embodiments, the signal generating unit comprises a radioactive marker, a fluorescent marker, a phosphorescent marker, a chemiluminescent marker or a labeling enzyme. Preferably, the labeling enzyme may comprise a horse radish peroxidase or an alkaline phosphatase.

In any one of the foregoing embodiments, the substrate is tetramethylbenzidine (TMB) when the signal generating unit is a horse radish peroxidase.

In any one of the foregoing embodiments, the kit further comprises a blocking solution. Preferably, the blocking solution comprises skim milk, bovine serum albumin, or casein.

In any one of the foregoing embodiments, the kit further comprises a wash solution. Preferably, the wash solution comprises PBS, TBS, PBS including a detergent, or TBS including a detergent.

In one embodiment, the present application provides a method for detecting a GM2-activator protein (GM2AP) in a biological sample, comprising the steps of: (a) applying the recombinant antibody or the antigen-binding fragment thereof mentioned in the present disclosure to said biological sample; (b) incubating said biological sample with a secondary antibody conjugated with a detectable label; and (c) detecting said detectable label.

In any one of the foregoing embodiments, the biological sample comprises whole blood, serum, plasma, urine, or a combination thereof.

In any one of the foregoing embodiments, the secondary antibody binds to a Fc domain of the recombinant antibody or the antigen-binding fragment thereof.

In any one of the foregoing embodiments, the detectable label comprises an alkaline phosphatase.

In any one of the foregoing embodiments, the step (c) is conducted by incubating said detectable label with a p-nitrophenyl phosphate solution and determining an absorbance at $OD_{405}$.

In any one of the foregoing embodiments, the step (c) is conducted by incubating said detectable label with a tetramethylbenzidine (TMB) solution and determining an absorbance at $OD_{450}$.

In one embodiment, the present application provides a method for inducing any one of the recombinant antibody or the antigen-binding fragment thereof mentioned in the present disclosure, comprising: (a) administering to a subject a peptide fragment comprising any one of the amino acid sequences of SEQ ID NOs: 1 to 4; (b) forming hybridoma cells; and (c) screening for a hybridoma cell secreting the antibody specifically binding to the glycosylated GM2AP.

In any one of the foregoing embodiments, the peptide fragment comprises the amino acid sequence of SEQ ID NO: 1.

DETAILED DESCRIPTION

Figure 1:
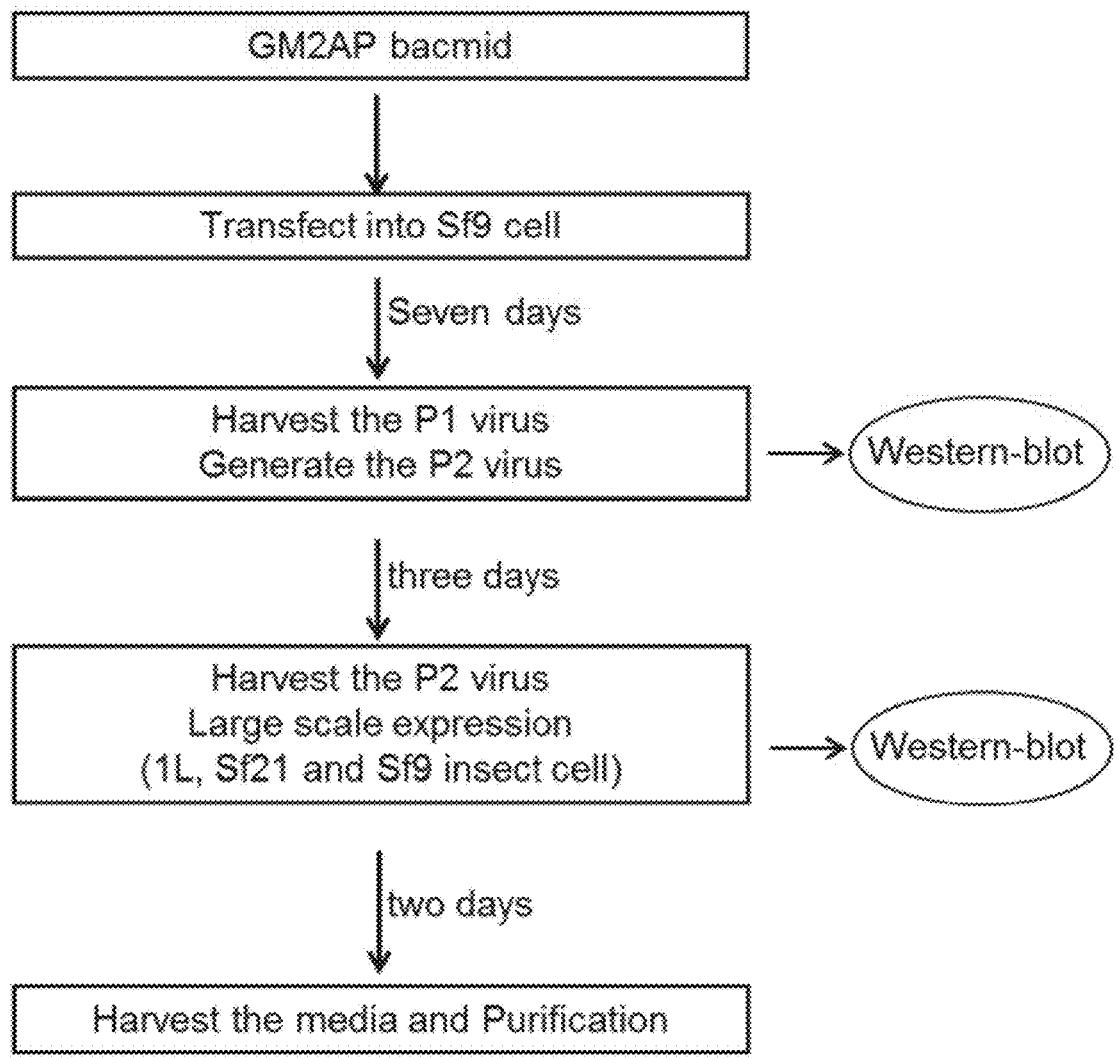
FIG. 1 illustrates a selection procedure for GM2AP monoclonal antibodies.

The foregoing and other aspects of the present disclosure will now be described in more detail with respect to other embodiments described herein. It should be appreciated that the invention can be embodied in different forms and should not be construed as being limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

As used herein, the terms "comprises," "comprising," "includes," "including," "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process, or method.

The transitional phrase "consisting of" excludes any elements, steps, or ingredients not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

Where applicants have defined an invention or a portion thereof with an open-ended term such as "comprising" it should be readily understood that (unless otherwise stated) the description should be interpreted to also describe such an invention using the term "consisting of".

As used herein, the term "about" is used to indicate that a value includes for example, the inherent variation of error for a measuring device, the method being employed to determine the value, or the variation that exists among the study subjects. Typically the term is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability depending on the situation.

The use of the term "or" in the claims is used to mean "and/or" unless explicitly indicated to refer to alternatives only or the alternatives are mutually exclusive, although the disclosure supports a definition that refers to only alternatives and "and/or."

The term "subject" as used herein refers to human or animals, including, for example, a mammalian subject diagnosed with or suspected of having or developing cardiovascular disease, particularly, myocardial infarction. Exemplary subject may be humans, apes, dogs, pigs, cattle, cats, horses, goats, sheep, rodents and other mammalians with the diseases that can benefit from the treatment.

The term "administering" or "administration" is referred to herein as providing an antibody of the present application to a subject. By way of example and not limitation, administration may be performed via parenteral, subcutaneous, intramuscular, intravenous, intra-articular, intrabronchial, intraabdominal, intracapsular, intracartilaginous, intracavitary, intracelial, intracerebellar, intracerebroventricular, intracolic, intracervical, intragastric, intrahepatic, ntramyocardjal, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal. For example, injection may be performed by intravenous (i.v.) injection, subcutaneous (s.c.) injection, intradermal (i.d.) injection, intraperitoneal (i.p.) injection, or intramuscular (i.m.) injection. One or more such routes may be employed.

The term "antibody" as referred to herein includes intact antibodies and any antigen-binding fragment (i.e., "antigen-binding portion") or single chains thereof. An "antibody" refers to a glycoprotein comprising at least two heavy (H) chains and two light (L) chains inter-connected by disulfide bonds, or an antigen-binding portion thereof. Each heavy chain is comprised of a heavy chain variable region (abbreviated herein as VH) and a heavy chain constant region (abbreviated herein as CH). The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each of $V_H$ and $V_L$ is composed of three CDRs and four FRs, arranged from amino-terminus to carboxy-terminus in the following order: FRI, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The "epitope" or "antigenic determinant" is a portion of an antigen molecule that is responsible for specific interactions with the antigen-binding domain of an antibody. An antigen-binding domain may be provided by one or more antibody variable domains. An antigen-binding domain can comprise at least one antibody light chain variable region (VL) and at least one antibody heavy chain variable region (VH). An antigen-binding domain can also comprise only VH or only VL regions. Specifically, in the present disclosure, the epitope could be a specific domain or a combination of domains of human GM2AP. In some embodiments of the present disclosure, the specific domains or combination of domains are of the human GM2AP that comprises the amino acid sequence of SEQ ID NO: 1.

The term "complementarity determining regions" ("CDR") are defined as parts of the variable chains in antibodies, where these molecules bind to their specific antigen. In this disclosure, the CDR regions in the heavy chain are typically referred to as CDR-H1, CDR-H2 and CDR-H3 and in the light chain as CDR-L1, CDR-L2 and CDR-L3. They are numbered sequentially in the direction from the amino terminus to the carboxy terminus.

The extent of the framework regions and CDRs has been defined according to Kabat et al. (see, Kabat et al., Sequences of Proteins of Immunological Interest, U.S. Department of Health and Human Services, 1991) and the ImMunoGeneTics database (IMGT) (see, Lefranc, Nucleic Acids Res 29:207-9, 2001; and online at imgt.cines.fr/IMGT_vquest/vquest?livret=O&Option=humanlg).

The "Kabat system" means in the context of the present disclosure the standard for numbering the residues in a consistent manner according to Kabat (1991; Sequences of Proteins of Immunological Interest, 5th edit., NIH publication No. 91-3242U.S. Department of Health and Human Services) and Chothia (1987; J. Mol. Biol. 196, 901-917). This numbering system is widely used by the skilled artisans and is based on sequence variability and three dimensional loops of the variable domain region which are important in antigen-binding activity. All the residues of the light chains or heavy chains have distinct positions in the Kabat system; i.e., the Kabat system applies to CDRs as well as to framework regions. The positions of specific residues of any antibody may be numbered according to the Kabat system. The rules to identify the CDR regions of VH and VL chains according to Kabat system are shown in www.bioinf.org.uk/abs.

The IMGT unique numbering system is an alternative to the Kabat System that allows one to compare the variable domains whatever the antigen receptor, the chain type, or the species [Lefranc M.-P., Immunology Today 18, 509 (1997)/ Lefranc M.-P., The Immunologist, 7, 132-136 (1999)/ Lefranc, M.-P., Pomrnie, C., Ruiz, M., Giudicelli, V., Foulquier, E., Truong, L., Thouvenin-Contet, V. and Lefranc, Dev. Comp.lmmunol., 27, 55-77 (2003)]. In the IMGT unique numbering system, the conserved amino acids always have the same position, for instance cysteine 23 (1st-CYS), tryptophan 41 (CONSERVED-TRP), hydrophobic amino acid 89, cysteine 104 (2nd-CYS), phenylalanine or tryptophan 118 (J-PHE or J-TRP). The IMGT unique numbering system provides a standardized delimitation of the framework regions (FR1- IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR—IMGT lengths (shown between brackets and separated by dots, e.g. [8.8.13]) become crucial information. The IMGT unique numbering system is used in 20 graphical representations, designated as IMGT Colliers de Perles [Ruiz, M. and Lefranc, M.-P., Immunogenetics, 53, 857-883 (2002)/Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., Tcell receptor and MHC structural data. Nucl. Acids. Res., 32, D208-D210 (2004)].

The term "antigen-binding fragment" as used herein refers to an antibody fragment, such as for example, a diabody, a Fab, a Fab', a F(ab')$_2$, an Fv fragment, a disulfide stabilized Fv fragment (dsFv), a (dsFv)$_2$, a bispecific dsFv (dsfv-dsfv'), a disulfide stabilized diabody (ds diabody), a single-chain antibody molecule (scfv), an scfv dimer (bivalent diabody), a multispecific antibody formed from a portion of an antibody comprising one or more CDRs, or any other antibody fragment that binds to an antigen but does not comprise a complete or intact antibody structure. An antigen-binding fragment is capable of binding to the same antigen to which the parent antibody or a parent antibody fragment (e.g., a parent scFv) binds. In certain embodiments, an antigen-binding fragment may comprise one or more CDRs from a particular human antibody grafted to a framework region from one or more different human antibodies.

Among the above antigen-binding fragments, a Fab, which is a structure having the light chain and heavy chain variable regions, the light chain constant region, the heavy chain first constant region (CH1), and bas one antigen-binding site. A Fab' differs from the Fab in that the Fab' has a hinge region including at least one cysteine residue at the C-terminal of the heavy chain CH1 domain. A F(ab')$_2$ is produced when cysteine residues at the hinge region of Fab' are joined by a disulfide bond.

An Fv is a minimal antibody fragment, having only heavy chain variable region and light chain variable regions. A recombinant technique for producing the Fv fragment is well known in the art. "Single-chain Fv antibody" or "scFv" refers to an engineered antibody consisting of a light chain variable region and a heavy chain variable region connected to one another directly or via a peptide linker sequence. A two-chain Fv may have a structure in which heavy chain variable regions are linked to light chain variable regions by a non-covalent bond. A single-chain Fv may generally form a dimer structure as in the two-chain Fv, wherein heavy chain variable regions are covalently bow1d to light chain variable regions via a peptide linker or the heavy and light chain variable regions are directly linked to each other at the C-terminals thereof. The linker may be a peptide linker including any 1 to 100 or 2 to 50 amino acids, and proper sequences useful therefor are well known in the art.

The antigen-binding fragment may be obtained using a protease (for example, a whole antibody can be digested with papain to obtain Fab fragments, or can be digested with pepsin to obtain F(ab')$_2$ fragments), or may be prepared by a genetic recombinant technique.

The terms "monoclonal antibody" or "monoclonal antibody composition" as used herein refer to a preparation of antibody molecules of homogeneous molecular composition. A monoclonal antibody composition displays a single binding specificity and affinity for a particular epitope.

The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences.

The term "recombinant" as used herein, is intended to include all molecules that are prepared, expressed, created or isolated by recombinant means, such as multispecific molecules (e.g. bispecific molecules) expressed using a recombinant expression vector transfected into a host cell, multispecific molecules (e.g., bispecific molecules) isolated from an animal (e.g., a mouse) that is transgenic for human immunoglobulin genes (see e.g., Taylor et al. (1992) Nucl. Acids Res. 20:6287-6295) or multispecific molecules prepared, expressed, created or isolated by any other means that involves splicing of human immunoglobulin and/or MHC gene sequences to other DNA sequences. Such recombinant multispecific molecules can include antigen-binding domains having variable and constant regions derived from human germline immunoglobulin sequences.

The term "recombinant human antibody" as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant human antibodies are sequences that, while derived from and related to human germline $V_H$ and $V_L$ sequences, may not naturally exist within the human antibody germline repertoire in vivo.

The term "humanized antibody" is referred to as an antibody that is generated from non-human species and comprises protein sequences that have been modified to increase their similarity to antibody variants produced naturally in humans. The humanization process could be necessary to avoid undesired immunogenic effect when applying a non-human source antibody in human. In comparison, the term "chimeric antibody" as referred to herein is an antibody made by fusing the antigen binding region (i.e. VH and VL) from one species with the constant domain with another.

The term "$K_{assoc}$" or "$K_a$," as used herein, is intended to refer to the association rate of a particular antibody-antigen interaction, whereas the term "$K_{dis}$" or "$K_d$" as used herein, is intended to refer to the dissociation rate of a particular antibody-antigen interaction. The term "$K_D$" as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art.

The terms "percent (%) sequence identity" or "homology" are defined as the percentage of amino acid residues or nucleotides in a candidate sequence that are identical with the amino acid residues or nucleotides in the reference sequences after aligning the sequences and introducing gaps, if necessary, to achieve the maximum percent sequence identity, and excluding conservative nucleic acid substitutions. Optimal alignment of the sequences for comparison may be produced, besides manually, by means of local homology algorithms known in the art or by means of computer programs which use these algorithms (e.g., BLAST P).

The nucleic acid sequences and the amino acid sequences mentioned in the following embodiments are summarized in Tables 1-3.

TABLE 1

Amino Acid Sequences of GMA2AP

| SEQ ID NO. | Designation | Sequences |
|---|---|---|
| 1 | GMA2A0 fragment | PIIVPGNVTLSVVG |

TABLE 1-continued

Amino Acid Sequences of GMA2AP

| SEQ ID NO. | Designation | Sequences |
|---|---|---|
| 2 | GMA2AP | MQSLMQAPLLIALGLLLAAPAQAHLKKPSQLSSFSWDN CDEGKDPAVIRSLTLEPDPIIVPGNVTLSVMGSTSVPL SSPLKVDLVLEKEVAGLWIKIPCTDYIGSCTFEHFCDV LDMLIPTGEPCPEPLRTYGLPCHCPFKEGTYSLPKSEF VVPDLELPSWLTTGNYRIESVLSSSGKRLGCIKIAASL KGI |
| 3 | GMA2AP | MQSLMQAPLLIALGLLLAAPAQAHLKKPSQLSSFSWDN CDEGKDPAVIRSLTLEPDPIIVPGNVTLSVVGSTSVPL SSPLKVDLVLEKEVAGLWIKIPCTDYIGSCTFEHFCDV LDMLIPTGEPCPEPLRTYGLPCHCPFKEGTYSLPKSEF VVPDLELPSWLTTGNYRIESVLSSSGKRLGCIKIAASL KGI |
| 4 | GMA2AP | MQSLMQAPLLIALGLLLAAPAQAHLKKPSQLSSFSWDN CDEGKDPAVIRSLTLEPDPIIVPGNVTLSVMGSTSVPL SSPLKVDLVLEKEVAGLWIKIPCTDYIGSCTFEHFCDV LDMLIPTGEPCPEPLRTYGLPCHCPFKEGTYSLPKSEF VVPDLELPSWLTTGNYRIESVLSSSGKRLGCIKIAASL KGIRHHHHHHHH |

TABLE 2

Amino Acid Sequences of the recombinant antibodies exemplified by the present application

| SEQ ID NO: | Designation | Sequences (Bold: CDR1; *Italic*: CDR2; Boxed: CDR3) |
|---|---|---|
| 5 | 21-2B5-F7 LCVR | DIVMTQTASSVYVTPGESVSISCRSTKSLLHSNGDTYLYWFLQRPGQSPQLLI YR*MS*NLAPGVPDRFSGGGSGTAFTLRISRVEAEDVGVYYL YATSTISFH VRC WDQAGAET |
| 6 | 21-2B5-F7 HCVR | EIQLQQSGAELVRPGTSVKISCMASGYSFTGYNMNWVRQSHGRSLEWIGN*IN PYFGSP*NYNQKFKGKATLTLDRSSNTAYMQLNRVTSEDSAVYYC ASRQLGL GDTMDY WGQGTSVTVSS |
| 7 | 21-4E3-C8 LCVR (mixed clone) | DIVMTQSHKFMSTSVGDRVTITCKASQDVSTAVGWYQQKPGQSPKLLIY*WA STRHT*GVPDRFTGSRFGTDYTLTISSVQAEDLALYYC QQHYITPWTF GGGTK LEIK |
| 8 | 21-4E3-C8 HCVR (mixed clone) | QVQLQQPGADFVKPGASVKLSCKASGYTFTSYWINWVKQRPGQGLEWIGN*I YPGSGS*TNYNEKFKNKATLTIDTSSSTAYMQLSSLTSDDSAVYYC$ RSTLYSY DDGS WGQGTTLTVSS |
| 9 | 21-4E3-C8 LCVR (mixed clone) | DIQMTQSPSSLSASLGERVSLTCRASQEISGDLSWLQQKPDGTIKRLIY*AAS*TL ASGVPKRFSGSRSGSDYSLTISGLESEDFADYYC LQYVSYPFT FGSGTKLEIK |
| 10 | 21-4E3-C8 HCVR (mixed clone) | QIQLQQSGPELGKPGASVKISCKASDYTFTDFYISWVKQRPGQGLEWIGW*IYP LDDHT*KYNEKFKGKATLTVDISSNTVYMQLSSLTSEDSAVYFC ARIYGYAMD Y WGQGTSVTVSS |
| 11 | 21-2H9-G2 LCVR | DIQMTQSPSSLSASLGERVSLTCRASQEISGDLSWLQQKPDGTIKRLIY*AAS*TL ASGVPKRFSGSRSGTDYSLTISGLESEDFADYYC LQYVSYPFT FGSGTKLEIK |

TABLE 2-continued

Amino Acid Sequences of the recombinant antibodies exemplified by the present application

| SEQ ID NO: | Designation | Sequences (Bold: CDR1; *Italic*: CDR2; Boxed: CDR3) |
|---|---|---|
| 12 | 21-2H9-G2 HCVR | QVQLQQPGADFVKPGASVKLSCKASGYTFTSYWINWVKQRPGQGLEWIGN*I YPGSGST*NYNEKFKNKATLTIDTSSSTAYMQLSSLTSDDSAVYYCSRSTLYSY DDGSWGQGTTLTVSS |
| 13 | 21-4G4-B11 LCVR | EIVMTQSHNHVHISGRQGHHHLQGQSGCEYCCRLVSTETRAIS*ITTDFT*GHPP GTLESLIAFTGSRSGTDYTLTISSVQAEDLALYYCQQHYITPWTFGGGTKLEIK |
| 14 | 21-4G4-B11 HCVR | QIQLQQSGPELGKPGASVKISCKASDYTFTDFYISWVKQRPGQGLEWIGW*IYP LDDHT*KYNEKFKGKATLTVDISSNTVYMQLSSLTSEDSAVYFCARIYGYAMD YWGQGTSVTVSS |
| 15 | 21-4B10-E1 LCVR | DIVMTSETHLCICHSWRVSLHLLQVYIESPAIIWRHLFVLVPTEARPVSSAPDI *SDV*QPCPRSPTQVQWRWVRNCFHTENQISGGTGCGCLLLYATSTISFHVRCW DQAGAET |
| 16 | 21-4B10-E1 HCVR | EIQLQQSGAELVRPGTSVKISCMASGYSFTGYNMNWVRQSHGRSLEWIGN*IN PYFGSP*NYNQKFKGKATLTLDRSSNTAYMQLNRVTSEDSAVYYCASRQLGL GDTMDYWGQGTSVTVSS |
| 17 | 22-2E9-G12 LCVR (mixed clone) | DIVMTQSQKFMSTSIGDRVSVTCKASQNVNTNIAWYQQKPGQSPKALIY*SAS YRYS*GVPDRFTGSGSGTDFTLTISSVQSEDLAEYFCQQYIGYPYTFGGGTKLEI K |
| 18 | 22-2E9-G12 HCVR (mixed clone) | QVQLQQPGATLVRPGASVKLSCKASGYTFINYWINWVKWRPGQGLEWIGN*I NPNCGV*TKYNEQIKSEATLTVDKSSSIAYMQLSSLTSEDSAVYYCPHLLLRWL LHVPFAMVYWGQGTSV |
| 19 | 22-2E9-G12 HCVR (mixed clone) | EVQLVETGGGLVQPQGSLKLSCAASGFNFNTYAMNWVRQAPGKGLEWVA R*IRTKSNSYATY*YADSVKDRFIISRDDSQSMLYLQMNNLKTEDTAIFYCVVTY WGFIYWGQGTLVTVSA |
| 20 | 22-3E6-B11 LCVR | DVVMTQTPLTLSVTIGQPASISCKSSQSLLYSDRKTYLNWLFQRPGQSPKRLI Y*LVS*KLDSGVPDRFTGSGSGTDFTLKISRVEAEDLGIYYCWQGTHFPQTFGGG TKLEIK |
| 21 | 22-3E6-B11 HCVR | EVQLQQSGPELVKPGASVKMSCKASGYSFTAYYIHWMKQSPEKSLEWIGE*IN PSTDDT*TYNQNFKSKATLTVDRSSRTAYMQLRSLTSEDSAVYFCARYGEGAY WGQGTLVTVSA |
| 22 | 22-4B11-B9 LCVR | DVVMTQIPLTLSVIIGQPASISCKSSQSLLYSDGKTYLNWLLQRPGQSPKRLIY *LVS*KLDSGVSDRFTGSGSGTDFTLKISRVEAEDLGVYYCWQGTHFPQTYGGG TKLEIK |
| 23 | 22-4B11-B9 HCVR | EVQLQQSGPELVKPGASVKISCKASGYSFTGFPHALGEAKSTKEPTVDWRD*I SIYWWY*YLQSEVQGQHIDCRQILQYSLYATQEPDITRLCSLLLCKIRRGGLLG PRDSGLCLC |
| 24 | 22-5B1-B2 LCVR | IVMTQSPKSMSMSVGERVTLSCKASENVGTYVSWYQQKPEQSPKLLIY*GASN RYT*GVPDRFTGSGSATDFTLTISSVQAEDLADYHCGQSYSYPLTFGAGTKLEL K |
| 25 | 22-5B1-B2 HCVR | EVQMQQSGPELVKPGASVEISCKASGYSFTGYYIHWVKQSPEKNLEWIGE*VN PISGGT*TYNQRFKAKATLNVDTLSNTAYMQLKSLTSEDSAVYFCARYGATD YWGQGTSVTVSS |

TABLE 2-continued

Amino Acid Sequences of the recombinant antibodies exemplified by the present application

| SEQ ID NO: | Designation | Sequences (Bold: CDR1; *Italic*: CDR2; Boxed: CDR3) |
|---|---|---|
| 26 | 22-5F2-E10 LCVR | EVQLQQSGPELVKPGASVKISCKASGYSFTGYYIHWVRRSPEKSLAWIGE*INPTTGGT*SYNQKFRAKATLTVDTSSSTAYIQLKSLTSEDSAIYYC ARYGEGAY WGQGTLVTVSA |
| 27 | 22-5F2-E10 HCVR | DVVLTQTPLTLSVTFGQPASISCKSSQSLFIITWKDIFVFGCYRGQASLQSAIS*FWCL*NWTLESLTGSVAVDQGQISHTRSTEWRLRIWEFIIA GKVHIFLR RTVEAPCWKSN |

TABLE 3

Nucleic Acids Sequences encoding the LCVR/HCVR of the recombinant antibodies exemplified by the present application.

| SEQ ID NO: | Designation | Sequences |
|---|---|---|
| 28 | 21-2B5-F7 LCVR | gtagatctgtgagcgagctgcgtagaatgagttcctgcgctgctgttgctctgactgaggcattgggatattgt atgactcagactgcatcctctgtatatgtcactcctgagagtcagtctccatctcctcagtcctactaagagtcctactgcat agtagcgacacttattgtatggtcctacagaggccaggccagtcagtctctcagtctctgatatcgatgtccaacctt gcccagagtccctgacatgacagttcaaccagcaccatccttcacgttcggtgctgggaccaagctgaggctga ggatgggtgttattacctgtatgcaacatccaatcttcccaccatcaatgtcaggaatccagtgatcctgaaacgg gtgatttgcaccaatgtatccatctccaccatcaatgtcaaggtggaagattgatgggacgaaaatggcctcagtgctgttcttg aacaacttctacccaaagacatcaatgtcaaggtggaagattgatgggacgcaaaatggcctcagtgctgttcttg actgatcagacagaagaagaacagcacccacacgagactcacaactcaccccattgtcaagagctcaacaggagtgtacgcg acagctacctgtgaggcctcccacacagacatcaactcaccccattgtcaagagctcaacaggagtgtacgcg |
| 29 | 21-2B5-F7 HCVR | tacaaagtaaccactcaaaggtaaaataatgcgaatttgccccccaagaagcagcagacgaagattgggtcatcct cttcctttctgtcagtaactgcagtgttctgatcctgttctgtgttactcattcactgcctcaacagtctgaagcctgggact tcagtgaagatatcctgcatgtctcttggttctactcatcactggctacgcactggaagcaaacatgggaagga gcttgagtggatcggaaatattaatccttacttttgtagtctaactacacaagttcaaggcaaggcacatttgactt tagacagatccccaacacagctcacagcctcaccagagtgacaagaacctcagtgactctgcagtcagtgacatcaa ggcagctccggctggagaatactcaatggactatggagccagtgtgttgaacaatcaaggttctacctctgcagcagctagat cccatcggtctatccactggccctgtgtgaggatacaagtgctcctggatcctgcagtgtacgatgtccatcgaggtgaacactactcgcagtctgac cccagccagtggatcgctaggtagtggatgtaggtgatcctgacctccctgtcaggtgtgcacacctccccatctgcaggctctcgcagtctgat ccatcccagcactcactctaactctaggtactgactcgaacctcagtcagctctcgcgctcacccagctcccagctcccacctgctctgcgct |
| 30 | 21-4E3-C8 LCVR (mixed clone) | gtgttcttccggttgtctgagtgtctgttggagacattgtgatgacccagtctccacacactcagtcctccacacagtggagacag ggtcaccacctgcaaggcacactcagtctgagcagcagtctagttggacactggtctgtggcttcagcaacatcactcccggtgacttcggtg aactactgatttactgggacatcaccactgcagtgcaactcctggcaacaactgtcagcaactctactcactccccgtgactcggtg gagcaccaagctgagaaatcaaacggcactcagtctccaacatcactctcccaccatgacgagcagttaacat ctgagggtgcctcagtcgtgtgttcttgaacaacttctacccaaagacatcaactacatgagcaacacctaacaaaggtggaagattgatgggcagtga acgacaaaatgcgctcaagagtcctgacagctgacgctgaacagttgacagtgactaacagtaccctgagggccactcacaagaccacccaaacttcaaccattccaac gttgaccaaggacgagtgacgaccagtatacctgtgaggccactcacaagaccacccaaacttcaaccattccaac gg |
| 31 | 21-4E3-C8 HCVR (mixed clone) | cgacagtctttttggttgcagcagctacaggtgtccaactcccaggtccaagtgcagcagctggtgtgacttgtgaagcct ggggcctccagtgaagctgtcctgcaagtcttggctacaccttcaccagctggatacatacccagaggtcaagcagagcct ggacaaggccttagtgagtggattcttatccgacagtcacacgcacagcactactgagactcaagaacaaggcc acactgactactatggaacatctcccacacgcctgcagtcagccgacactctgacgactctgcgtctactact gttcaagatcaactctgtctatcaactggcccctgactgtgctgccaaaactaactcatgtgacctgatgctggtcaagg cacccccatctgctactggtctcagcgactctggaacttgtgaactcccagtccaccttccagggtgaccccttccagcagtcctgca gtctgacctctcacactctgagcagctcgcagtgacagtgactctgcagcagcgcaggagaccgtcacctggaactgc cctccc |
| 32 | 21-4E3-C8 LCVR (mixed clone) | tgttgctggtttccaggtatcagattgacatccagatgacgcagtctccatccctctattcgcgtctctgggagaaagag tcagtcacttgtcggcaagcaggaaatagttagtggcagcacatagtgcttaagcgactcagcagaaacagaactaattaaacg cctgatatacgccgcatccacttagctctgtggtcccaaaaggttcagtggcagtggtagcagtcctgggacgatttcactctctcac catcagcagcctgcgctgaagatcgagattttgcagcatatacttatctacaatatgctagtcatcacgtcggctcggggacga agttggaaataaaacgggctgatgctgcaccaactgctcaccatcctcccaccatccgatgagcagttaaactgtaaactgaaactggaggtg |

TABLE 3-continued

Nucleic Acids Sequences encoding the LCVR/HCVR of the recombinant antibodies exemplified by the present application.

| SEQ ID NO: | Designation | Sequences |
|---|---|---|
| | | cctcagtgtgctgtcttctgaacaacttctacccaaagacatcaatgtcaagtggaagattgatgcagtgaacgacaaaa tggcgtcctgaacagtgactgatcaggacagacagacgcacctacagcagtgagcagcagcccctcacgttgaccag gacgagtgacgacataacgctatacctgagccactcacatagacagcaatctcacccattcaacag |
| 33 | 21-4E3-C8 HCVR (mixed clone) | ttgaacttgccattcctcctgtcaggaactgcaggtgccattgccagatgccagtgcagcagtctgaactggga agctggggcttcagtgagatccctgcaaggctctcagatctcactgactctctataagtgggtgaaacagagg cctgacaggggacttgagtggattggagattatcctttagacgatcatactaagtgagaagttcaagggccaag ccacattgactgtagacatatcctccaacactcagcagcctacagctgaccctgagatctgggtctatttc tgtgcagaatcatgatgctactggatactgcattgtggagaataacctggctcctcggtgacttaggatgcctggtcctgcaaacaacagcc ccatcggctctatccactagccctgtgtgtgaaatctgattcctgcagtggtgcacactttcagctgacctgcagtctgacctg ctgagccagtgacctgacctgagctgtaacctcgaccctgacctggcccagccatacacctgaagctcagagacggtccccc ctacaccctcagcagctcagcgactgtaacctcgaccctgagccccatcacaccctgagacctccagacctcagacggtccccc |
| 34 | 21-2H9-G2 LCVR | gccgtcatctgcacgatcatgaggtacctcgctcacgtgcttaagattcttgtcagctctggttccagtatcagatgtga catccagatgaccagctcccatcctcttatctgctctctgcaggaacccagcttgagaaagtcagtcctttaagtcgggcaagcaggaa attagtggtgactttagccggcttgcagcaagacaagtattctccaccatctaccgccgccatccacttagctct ggtgtccaaagttcagtgcagtagtagtgtgatccagcagcctgcgcagcctgaacagattcaacagcagagat tttgc agactattactgtctacaatattagtatcaacatcacgttgcgcgcggacaaaggtggaataaaacgcgctgatgctctgc accaactgatctcattccaccatccagtgagcagtaacatcgagagtgccccagtgcgcgctgtcttgaaactcctca cccaaagacacatcaaatgtgcaagtggagagttgatgcagtcagtgacaaatggcgtccgaacagttgactgatgcagg acagcaaacagcacctgacagacgcatgagcagtggagcagctaccgtgacaagcgagtatgagcacgatgaacagctataac ctgaggccattcaccagaacatagtttgcccatcaaccagttgtagagggttccaacaagagaatgaagacccaaac aaaaaaaaaac |
| 35 | 21-2H9-C2 HCVR | cgtctgtctttggtgcagcagctacaggtgccactcccaggtcccaactgcagcagcctggtgctgacttgtgaagcct gggcctcagtgaaggctgtccagaaggtctcccaaggctccacttccacagctactcagcctgataaactgggaagcgagaggcct ggacaaggcttagtgattggaaatatttacctgtacggctacatgtgctcaggcacctgagatctgcgtactact gtcaagataccaacctctataatggttacagacgacggcctgggaccaaggcaccactccacagtctcctccagcaaacga caccccagatctgcgccctgatctgcccgccccaaactaccctgaccctgacctggcacactttccagcctgactgtcaag ggctatttccctgacctcctacaactgacgctgctcgcacgctgctgacacctccctggccccagccgagccctgtcctgc atctgacctctacaactgagcagtgacagctgactgtcccagtgactggcaccccagcagcactctccacctgcaacgtg cccgtcca |
| 36 | 21-4G4-B11 LCVR | gactagagcacgtggtcgtctggtgttgacggagaaaattgtgatgacccagtctcacaatcatgtccaacatcagtggagac aggtcaccatcacctgcaaggccagtcaggccagtagtgagtactgtgtacctgtagaacccaggcaaatctcc taacttaccgtccaccactgggcatccaccgagcagaagaccctggaccgcttcacgagtaagatatcgcgtgagactt atattctcaccatcagcagtccgaaatcaacaaccggcctgatgagtgaaactccgccaccatccgatcagcagtta gtgaggcaccaagctgcctcagtgcgtgtgcttctgaacacctttgactaggacagcaagacagcacctacagcagacaccctc catctggaggcaaaatggcgtcctgaacagttgactgacattaaccctatacctgaggccactcaacgactccaccatcgtc agttgaccaagtgactgtatgaacagacacatgacacttatacctcaccgcaggaaaaaaaaaaaagcggaaggacggcggtaa aagagcttcaacaggaatgacttagggggggaaacatattcaatctttcttccgggggcgggaaagg |
| 37 | 21-4G4-B11 HCVR | catgaatgaatgctgggtcattctttctccctcgcaggaactgcaggtgtccattgcagatccagtgcagctggac ctgaactgggggaagctcggggcttcagtgaagatatcctgcaaggcttctgactactcactgactctatataagttgg |

TABLE 3-continued

Nucleic Acids Sequences encoding the LCVR/HCVR of the recombinant antibodies exemplified by the present application.

| SEQ ID NO: | Designation | Sequences |
|---|---|---|
| | | gtgaaacagaggcctgacaggactgagtgactgatggatttatccttagacgatcattactaagtacgacctgagaagt tcaagggcaaggccacattgactgtagacatatcccaacagtctactgctactgcagctgactggagctcctgaggact ctgggtctattctgtgcagaatctatggatgtatgactactgggtcaaggaacctcagtcactacgctcctctcagcc aaaacaacagcccatcggtctatccactggcctgtgtggagataacaactggctcctggtgactgactctaggatgcctg gtcaagggtatttcccgagcctgaggtgctgaccctgaccctgagctcagtggtgtgcacacctccccagctgt cctgcagctgacctctgacctcacacccagctcagtgactgactgtaacctcgagcccagtgccagtccatcacctgcaa tgccccgcag |
| 38 | 21-4B10-E1 LCVR | gcccccttttatggggggggaactgcctcagtccttgctgctgtcttgcctggatcctcgagctcagtggg gatattgatgacttcagaaaatccactctgatatgtcactcctgagagtcagtctccatctcctgcagtctactaagagt ctcctgcatagtaatgcgacacttgattggttcctacagaggccaggcagctctcctgcagtctgatactatcggatg tcacctgccccaggtagtccccagctcagtggctgtggttcaggaactgcttcactctcacactcagtgaat gaggctgaggatgtgggttgttatgtactgtcaactctgtaatatcctcactgagcagtagatctcagatgcttaacat cggagttacatcggagtgcccagtgtgt aaacgggctgatgtgcaaaactttaccccaaagacatcaagtcaaatgcaagctcaagcagacagcaacctcaccccttaa acgtggacttgccctggcacaggcctgccacagcctaaaaaacatcatcactaacttcaccattcaacggg |
| 39 | 21-4B10-E1 HCVR | agcctctccccccccaaagagagggtgacctgctatctcctttgtcagtaactgcaggtgtccactgtcgatccagctgc aacagtctgaactgagctggctgaggctgagggtgagcagcatgtcagtgaagatatccagttggattactcattcactggctac aatgaactggtgaggcaagccacatttgaaggatccgaatacctactcactcactcacagaagagga catctggagactctgcagtctactctgcatcaagcagcgccacgggctctactcccactagcctgtgagatactgggtcaaggaa cctcagtcaccgctccgctcctcagccaaagatgcctggtgctactcaagggtatttccctgaccccgaccctgtccgt gggtgcacccctcgcgacgctccgacctcagcagtcgctgactctaaccctagactgaccctgcgaccctggc ccagctcagtcgcgtcgcactcgtgttca |
| 40 | 22-2E9-G12 LCVR (mixed clone) | ggtcatactgctgtgtctgtgtctggtctgtgatgagacattgtgatgagacagtctccacatcatgtccacatcaataaggaga cagggcagccgtcacctcagcatccaggccagcagatgtgaatacataaagcctggtatcaacagaaaccaaggacaagtctc ctaaagcactgatttactcggctgatgtgatccggctttgagcttcagtccagtcgtcagcagatatcgatcttggagacagattct cacagctccatcagcgatcagcgtcgagtgcagatgctgccatatatctgtcagcaataattctctcccaactcgagcagtta aaggggacccaggtctcgatgctaaaaacccgggctgaaatacaaacctggagatagaagacagcaataatgacagtgagtagt catctggagctgcctcaagtgtctctgatccgtgactgactgactgatcagacagcaagacagcacctacgcagatgagcagacccctc gaacgacaaaatggcgtcctgaacagtgacataactatacccgtgaggccactcaacagtggaggcactagacttcaccattgtc aagagctcaacaggaagtgagtgaaccc |
| 41 | 22-2E9-G12 HCVR (mixed clone) | gggtcatctctcttggtagcaactgctacaggtgtccactccaggtcgcagctgcagcggtgagtgatggctgac gctgggcttcagtgaagttcctcaaggcttcctgcaaagcttctggctaccacttcatcaactactgatgaaactggtggaagtggagg ccacactcaaggcctgactggatggaaatattcaatggctggttactaatcagcagctgtgctgcgagactcgatctcagctcattatta ctgtctcattattactacgatgttgctcaccgcccatcggtctataccactggtgctcacgcccctggactctcgatgggttcactgtctacctcagccagttctattta tcagccaaaacaacagcccatcggtctatccactgccctggccctgagctacagaaaacagtggccacgcctggtcttcgcgacttagga tgcctgtccaaggttcctcgatattccctgaccgacctgtgacctgttacctggagactgttgtgctgcacccttcc agctgtcctgcagctgcacctctaccacctccagcagtgactgactctaaccctagacttgactctgacgcaagccagccagtcatcac ctgcaattggccctcccca |

TABLE 3-continued

Nucleic Acids Sequences encoding the LCVR/HCVR of the recombinant antibodies exemplified by the present application.

| SEQ ID NO: | Designation | Sequences |
|---|---|---|
| 42 | 22-2E9-G12 HCVR (mixed clone) | gtgggtcaatatacattgtcatgtcttaggctgaagtggttcttcttgttgttttttatcaagtgtgcattgtgaggtgcagctgtgtgagactggtggaggattgtgtgaggtcccaggtcattgaaactccatgtggccctctgattcaacttcaatactatgcatgaactgcccgccaggctccaggaaaggggtttggaatggttgctcgcataagaactcaaaagtaatcttatgcaacatatatgccgattcagtgaaagacacagtctcccagagatgatctccaaagcatgcctatctgcaaatgaacaacttgaaacttgaggagccaaaacaaacagcccatattttactgtgtggttacctactgggggttcttactgggcaagtgctcctcggtcactgtctccgagccaaaacaaacagcccatattttactgtgtggttacctactgggcctgtgtgtgagatacagtggtctccggtgactctaggatgcctggctgcaagggttatttccctgagcctgacctgacctgagcctggaagctctggatcctgtcctgtcagtgcacacccccagctcctgcacacctgaacctcgagcacctgcagccagcacctcaactcgagcacctgaacctcgagcacctgcagccagcacacctcaactcagctccagcacctcaactcagctcctgcacacctgaacctcgagcacctgcagccagcacacctcaactcagctcctgcacaccccttgcacccccaactcagcaacacacgccaacaccgccaacaccgccaacaccg |
| 43 | 22-3E6-B11 LCVR | agtcaacaacaacaaaaaaaaagatcaaaatctacaacgtgacgggaggtgggggaggagcagtgctctttttaggggggacactgttggtgcctgacctgtctcggatctcggagctgcaccagtggtgatgaaccagactccaccacttgaggttacccaccagccaaccagcagcctccatcttcgcaagcctcatatctgcaagctcagacctcagcctctataatctgagatagaagacatattgaattggtttcagaggccaggcagatcagggacagatgagatcgggagatcagcaggtcaccaccactattccaagcctaatctatctggttcctcagcagctgagacggagtccgagagcttgtcgagcctcgtgagcacgtgcaccacccctgagcactagcaaatcacactgaagcagatgggctcctgcgcagaggttcagtgcttgccctcaattatgtctgccaccactccaccaccctcagctgagccacgtcactgcagacggaccccctgagcactagcaaatcactgcaccttgcacacgtgcctaagccattgggctgatctcactcttcaagcccaagctatctgcaccaccctgaacttaccaagttcaccacaccctgatagctcacgctactcaccacccgctaccaccctcagctggagcactcctgaacccatctgagaatctcagtacgacactcttacccgatcgctgcctactaccacgatgcagcagtcaacaacttgagcacaaaacgaccacaaagacccagcactgaagcgaataa |
| 44 | 22-3E6-B11 HCVR | gtaggagctggttcctcttaatcctcagtaactacacaggtgtcccactctgaggtccagtcagctgacctgagctgtgaaagggaagggcctcaagctgacggttaccttcagtggtgaattaatgcatctggatttactgagggattaatcagagccaaattgatcagtagcactgatgacacaaccacagaacttccagtccaaggcacactgactgactgactgactgactgactgactgagcctgactctgaaaaagacctgggcggcggcggcggaagcctgagaactagtgaacctggacctgctctaacggccaaccgctgagggagcctgagggacctcgagctcgatggaagcctgagggacctcgagctcgatggaagcctgactaactgactgactgagctcagcctgactctgaggcctgactatggaagcctgactaactgactgactgactgagctcagcctgactctgaggcctgactatctatcctgcgggttgtgaccttcatcgagggacctccgctgaggagcctgaacaggcccagcatgcccaagttcatctgcaagtccaagtccaacacactgccgaagaagcccacagtgttcacgctgcaagtccaagttccagctctgaggtctcacactcttacagtatcctgcgacactcgctgtactctcccaaagcctaagagcagctagcctgcacactgcctgaaggctccctctacagtatcctgcgacatctcctagtgaagctagcctagatgctgagttgcaccagcaagagcaccgctgcctgcctgggtactccacctagcactggcagcctgcgtttgcctgcactttctttctctactcaccacccgcctccctaacgctctcctcctccagctctctcactcccgacgagctgcagactcatccactactgctcactctccgtccccgcctgctccagtgctgtactaccctctacgcgctagcttccctgcgcctgtctcccacctgctctccacaccgtgcccaggcccctcactcttcgtcacgctgacgaacgagctgtcccaagctggactcatgagggggagcctgttccagtctaacccatggccactgcccaccccgctgcccgctcgagttccctgccctgactgaaccggaccgtcacccctgactcagcgtaccgccgctgtctgaacaggaggaactaactctgaatctggccggcaatgagttcaccgtgcatccgacttcaactcctcgctggcgct |
| 45 | 22-4B11-B9 LCVR | gcatcgcttaacacgtctcgtcttattttgctacacgtcttcggttatacgaggtgccctacgcttcgggtatcgttgacatgaaatgcccagtcatgccgtgggtaagcttggacactgaagcttaagcctgacagttgacactgacgtgaactaacatgccagttgcttgcattcactttaggcgggcggcaaccactgcaacatagtcttttgcttttatttataggcggcaaccactgcaacatagtcttttgcttttatttataggcggacagcacgcgtgtgatgcagcagatattgacactgtgagtactcggttcattgacctcgttcattgcaggtttgttacagggccgcagtgtgttacagaggcccagtttatttgacctgtccactaggcctgtgcaacccccgcgtcggaagacacatatttgaattggttgtacagggaacgttggcggcacaggccaaccactccaccactggcccaccgagtatgtggccgagcactgcctagcagtggccccggctccatgctcaaactgactgactggaggttttattatgctgcagatacacatttccgacctgcagacactgcagactgcagaggaactaccattcaagctgacagcagaacatggcagtgacgacaaaggcgtcgggagcctcttgatggaggtttgggagctgcacagtgacgtaatcaaagagaagcactgcctgcctgggaagctgtgacccgtacgctgaggcactaggccactagcccgaggccccgcgtcgacacagccagcgacctcagtcagtggtgcctcttgaaacactctgaacagttgacgtgatcaggagccagaggagcagcagagcactacagtggcactacgacgtgaactaccattcaagctgacagcagaaacatggcagtgacgacaaaggcgtcgggagcctcttgatggaggtttgggagctgcacagtgacgtaatcaaagagaagcactgcctgcctgggaagctgtgacccgtacgctgaggcactaggccactagcccgaggccccgcgtcgacacagccagcgacctcagtcagtggtgcctcttgaaacactctgaacagttgacgtgatcaggagccagaggagcagcagagcactacagtggccggcaatgatcactgcctgcacacttgaccaaggacgagta gggg |
| 46 | 22-4B11-B9 HCVR | acggtaatgaaagaaggggggtggacctggttttttcgcgtttttttccaccttttaaaattgggggtaaaaccccccccttttcaatgagaacctggcttttattttaatcctgtcagtaactacacaggtgtccactcgtcagtaactacacaggtgtccactcgactgagctggtgaagcctggggctgggcgcagattcctcaaggctcggattcactggttactcactggtttcctcatgcacatt |

TABLE 3-continued

Nucleic Acids Sequences encoding the LCVR/HCVR of the recombinant antibodies exemplified by the present application.

| SEQ ID NO: | Designation | Sequences |
|---|---|---|
| | | tgggtgaagcaaagtcctgaagtgagctgcctgagtgattggagagattaatcctagtactggtactaccactgaga ggtcaaggccaaggccacattactgtgcaagatacggcaggggggcttactgggcaaggactctgtctctgtctgcggca acctgcagtctattactgtgcaagatacggcagggggcttactgggcaaggactctgtctctgtctgcggca aacaaacagcccatcggtctatccactggccctgtgtgaagatacaagtggctcctcggtgactctaggatgctgg tcaaggtgtattccctgaccgcagctgacctgacctgaactggatcctccagtggtgcacaccttccagctgtc ctgagtcttgacctctgacctctacccctcagcagctcagtgactgactgtaacctcgagcactggccagtccatcactctgata aatcttgcaag |
| 47 | 22-5B1-B2 LCVR | ctgtctatgcctgcagacatgacagtcagagatgagttacatcatcagaagatgcttatgatattcgatgttcgataa caatgcatgacaaacctcttgctgacatgtagtatgatcctacggtccacgtcagtgatctactatgcaagacgaaagaacagatgct acatcaaactccttggtgcaggtcattactcctttgatgatgtactttgcataaagttctagagggcagaccagctgtt ccatgattataaacctaggccttctccacggagatctcaaagcatcataactcactggggggccccctcaagtg ggggggggaggaggccttatctcctgctctgtctgttgggggcagtagaacgttaatgaccatctccaa atccatgccatgcagtcagtgagagagggtcacctgagctgcaaggcagtgagaatgtggtactatgtatcctggtat caacagaaccagcagtctctaactgctctgataccggatccatccaaccgtacaagctacaactggtgatctgcttcac agcagtggatcagcaacagatttcatctgacctgatctgaggctgaaggcgtgaacctgcaccaactgtatccat gagttacagctatccgctcacgttcggtgcggagaccaagctggaactgaaactcgtgtctgtcttcatcttcccgccatctgatgagc ctcccaccatccagtgagcagttaacatctgaggtgctctgcagtgctgtctgtgaacaactctacccccaaagacatc aaagtcaaagtggaagattgatggcagtgagcagacacaaataatggctgctgaacagtgactgactaacagcagacagaaagac agcaccttacagctgacagcagcacctcacgttgaccaaggcagtgagtataacaagactataccttaggtccacttcaagg ctcaccaagcacttcaccccattcaagg |
| 48 | 22-5B1-B2 HCVR | gtattatgtgaggtgtcttttcctggtgtcttcatcctattgtctctgcatcgattttcttttttatacagcttcttgtactcagt attatattagtattgcatatgcattttctttcttatctttgttttcgtaattcacggggtaatcggactgtagaaagctgttgagattt gctttttaggtttgcttaattaggatgctattgatcctgagttgatttatattactcattcgaattgaacagtaagct ctatgagattcttgtacaaggttcgcaaggagcatctgcttcttttgttgttgttgtatagt ggaagattttaaacattcgctaaaagcagcaaagatatatagaaaaagtgttgaactggcttgttgtttaatcctgtca gtaactcaggtgtccactctgaggtccagctccagctccagctctcactggtacttatcatgtgatcacactggtgaagcaacttgaatggatt gggagagttaatcctattagtagtgtacctacctacaaggcaaggcaagtcaagtgacatgtgaacacattat ccaacacagctacatgcagctcaagacctcagtcctcagccaaaacagcccatgggccctgtattcgccggtcagtgactgaa actattgggtcaaggaaccctcagtgcctgcagcctcctctaggatgctgtagcctgtcaaggtatttcctgaccgcagtgacctgaa gctgagatacaaggtgtctcctggttcgcacacctccagtgggcctgcctgctcaccctcaccgccaggctcagtgactg taacctcgagcacctggccagtccagtcgtctcaaaacctgaagaactgtgca |
| 49 | 22-5F2-E10 LCVR | ttacaaatacagataagcgtttccattacaactaaacataaaaattattggtcgtaacgctctttttttttgggggaaccaagtt gctgttaggctgttgctgtctgttctttggatctgatcagatacctggatacgcaaggatgtgctctcactcacttgtcggttac cttggcaacaccaagctcctcctctcctcagctcagtcggatctcgaaagcatcctcgtctgcaagagtcccttaattagaagtgatgagaagacattattatgtgactctgtggtttcagtg acagagccaggtcagagttcacactggacaggattcaactagtggaactgtcggagttggatttgggagtggcttgtggcttgggcaagt cagattttcctccagttactacctgtggaagctctaaactgagagctgaggatttggagtcgtgtagccaactcatcttcc caccatccagtgagcagctaacatctgaggtgcctgctctgcagtgtctgtcttgaacaactctcacccccaaagacatcaagtc aagtggaagattgatggcagtgagcagacacaaaatggctgctgaacagtgactgactaacagcatgaacagacagcacct acagcatgagcagcacctcacgttgaccaaggacagtgagtataacaagactataccttaggtccacttcaagg actataccttcaccccattcaagtg |

TABLE 3-continued

Nucleic Acids Sequences encoding the LCVR/HCVR of the recombinant antibodies exemplified by the present application.

| SEQ ID NO: | Designation | Sequences |
|---|---|---|
| 50 | 22-5F2-E10 HCVR | acatacaatcaatcgaacatacacaaaacattacccctcttaaaacattcgttacacctccctactcccccccgatgagtc gccgggcttatttaaatcctgtcagtaactacagtgtccactctgagtccagtcgagcagtcctgacctgaactggtg aagcctggggcttcagtgaagatatcttgcaaggctctggttcactcattcactggtactacatacactggtgaggcgaa gtcctgaaaagagccttgctgtgattggagagattaatcctaccactggtgtacttcctacaaccagaaattcagggcca ggccacattgactgtagacacgtcgtccagacagcctatattcagtcaagagcctgacatctgaggactctgcaatctat tactgtgcaagatacggcgaggggcttactggggcaaggactctggtcactgtctctgcagcaaaacaacagccc catggctctatccactggcccctgtgtgtgagactggggctccctcgtgactgactctaggatgcctggtcaaggttatt tccctgagccagtgaccttgacctgaactgtcggatccctgtccagtggtgtgcacacctcccagtgtcctgcagtctga ccctacaccctcagcagctcaacctgacgtcagtgactgacgtaacctgccaacctgccagtccatcacctcatacgacctgctaa |

Certain exemplary embodiments according to the present disclosure are described as below.

Recombinant Anti-GM2AP Antibody or the Antigen-Binding Fragment Thereof

According to one embodiment of the present disclosure, the present application provides a recombinant antibody which specifically binds GM2-activator protein (GM2AP) (the "anti-GM2AP antibody") or the antigen-binding fragment thereof. The GM2AP of this embodiment may comprise an amino acid sequence of SEQ ID NO: 1, SEQ ID NO: 2 or SEQ ID NO: 3, or SEQ ID NO: 4. The anti-GM2AP antibody or the antigen-binding fragment thereof of the present embodiment may specifically bind to one or more amino acid residues within amino acids 1-14 of SEQ ID NO: 1 or the amino acids 57-70 of SEQ ID NO: 2 or SEQ ID NO: 3. Preferably, the anti-GM2AP antibody or the antigen-binding fragment thereof may specifically bind to GM2AP among amino acids 57-70 of SEQ ID NO:2 or SEQ ID NO: 3. In other words, said amino acids 1-14 of SEQ ID NO: 1 and amino acids 57-70 of SEQ ID NO: 2 or SEQ ID NO: 3 form the epitope of the anti-GM2AP antibody or the antigen-binding fragment thereof of the present embodiment.

As used herein, an antibody that "specifically binds to GM2AP" is intended to refer to an antibody that binds to GM2AP with a binding value KD of less than $1\times10^{-8}$ M, less than $1\times10^{-9}$ M, less than $1\times10^{-10}$ M, less than $1\times10^{-11}$, or even less.

The anti-GM2AP antibody or the antigen-binding fragment thereof may comprise a light chain variable region (LCVR) and a heavy chain variable region (HCVR). In some embodiments, the LCVR may comprise an amino acid sequence having at least 80%, 85%, 90%, 91%, 92%, 93%, 94%, 95%, 96%, 97, 98, 99%, or 100% (or any percentage in between) identity to SEQ ID NO: 5, 7, 9, 11, 13, 15, 17, 20, 22, 24 or 26. Meanwhile, the HCVR may preferably comprise an amino acid sequence having at least 80%, 85%, 90%, 91%, 92%, 93%, 94%, 95%, 96%, 97, 98, 99%, or 100% (or any percentage in between) identity to SEQ ID NO: 6, 8, 10, 12, 14, 16, 18, 19, 21, 23, 25 or 27. More preferably, the pair of LCVR and the HCVR may comprise the amino acid sequence pairs having at least 80%, 85%, 90%, 91%, 92%, 93%, 94%, 95%, 96%, 97, 98, 99%, or 100% (or any percentage in between) identity to SEQ ID NOs: 5/6, 7/8, 9/10, 11/12, 13/14, 15/16, 17/18, 17/19, 20/21; 22/23, 24/25 or 26/27, respectively.

Moreover, said LCVR may comprise three light chain complementary determining regions (LCDR1, LCDR2 and LCDR3). Each of LCDR1, LCDR2 and LCDR3 may comprise an amino acid sequence having at least 80%, 85%, 90%, 91%, 92%, 93%, 94%, 95%, 96%, 97, 98, 99%, or 100% (or any percentage in between) identity to SEQ ID NO: 51, 52, 53, 57, 58, 59, 63, 64, 65, 69, 70, 71, 75, 76, 77, 81, 82, 83, 87, 88, 89, 96, 97, 98, 102, 103, 104, 108, 109, 110, 114, 115, or 116. Meanwhile, said HCVR may comprise three heavy chain complementary determining regions (HCDR1, HCDR2, and HCDR3). Each of HCDR1, HCDR2 and HCDR3 may comprise an amino acid sequence having at least 80%, 85%, 90%, 91%, 92%, 93%, 94%, 95%, 96%, 97, 98, 99%, or 100% (or any percentage in between) identity to SEQ ID NO: 54, 55, 56, 60, 61, 62, 66, 67, 68, 72, 73, 74, 78, 79, 80, 84, 85, 86, 90, 91, 92, 93, 94, 95, 99, 100, 101, 105, 106, 107, 111, 112, 113, 117, 118 or 119.

More preferably, the LCDR1/LCDR2/LCDR3 may have the amino acid sequences having at least 80%, 85%, 90%, 91%, 92%, 93%, 94%, 95%, 96%, 97, 98, 99%, or 100% (or any percentage in between) identity to SEQ ID NOs: 51/52/ 53, 57/58/59, 63/64/65, 69/70/71, 75/76/77, 81/82/83, 87/88/89, 96/97/98, 102/103/104, 108/109/110 or 114/115/ 116, respectively. In addition, the HCDR1/HCDR2/HCDR3 may have the amino acid sequences having at least 80%, 85%, 90%, 91%, 92%, 93%, 94%, 95%, 96%, 97, 98, 99%, or 100% (or any percentage in between) identity to SEQ ID NOs: 54/55/56, 60/61/62, 66/67/68, 72/73/74, 78/79/80, 84/85/86, 90/91/92, 93/94/95, 99/100/101, 105/106/107, 111/112/113 or 117/118/119, respectively. Still more preferably, the LCDR1/LCDR2/LCDR3/HCDR1/HCDR2/ HCDR3 may have amino acid sequences having at least 80%, 85%, 90%, 91%, 92%, 93%, 94%, 95%, 96%, 97, 98, 99%, or 100% (or any percentage in between) identity to SEQ ID NOs: 51/52/53/54/55/56, 57/58/59/60/61/62, 63/64/ 65/66/67/68, 69/70/71/72/73/74, 75/76/77/78/79/80, 81/82/ 83/84/85/86, 87/88/89/90/91/92, 87/88/89/93/94/95, 96/97/ 98/99/100/101, 102/103/104/105/106/107, 108/109/110/ 111/112/113, or 114/115/116/117/118/119, respectively.

The anti-GM2AP antibody or the antigen-binding fragment thereof, as used herein, can be a diabody, a Fab, a Fab', a F(ab')$_2$, an Fv fragment, a disulfide stabilized Fv fragment (dsFv), a (dsFv)$_2$, a bispecific dsFv (dsfv-dsfv'), a disulfide stabilized diabody (ds diabody), a single-chain antibody molecule (scfv), an scfv dimer (bivalent diabody) or any combination thereof. Moreover, the anti-GM2AP antibody or the antigen-binding fragment thereof can be a monoclonal antibody, multispecific antibody, human antibody, humanized antibody, chimeric antibody and any combination thereof. Preferably, the recombinant antibody or the antigen-binding fragment thereof is a human antibody.

Polynucleotides Encoding the Anti-GM2AP Antibody or the Antigen-Binding Fragment Thereof, and Vectors and Host Cells Comprising the Same According to one embodiment of this disclosure, the present application also provides a polynucleotide encoding any one of the anti-GM2AP antibodies or the antigen-binding fragments thereof mentioned in the present disclosure. The polynucleotide may comprise a nucleic acid sequence having at least 80%, 85%, 90%, 91%, 92%, 93%, 94%, 95%, 96%, 97, 98, 99%, or 100% (or any percentage in between) identity to SEQ ID NOs: 28-50. In some embodiment, the nucleic acid sequence encoding the LCVR of the recombinant antibody of the foregoing embodiment or the antigen-binding fragment thereof may have at least 80%, 85%, 90%, 91%, 92%, 93%, 94%, 95%, 96%, 97, 98, 99%, or 100% (or any percentage in between) identity to SEQ ID NOs: 28, 30, 32, 34, 36, 38, 40, 43, 45, 47 or 50. Meanwhile, the nucleic acid sequence encoding the HCVR of the recombinant antibody of the foregoing embodiment or the antigen-binding fragment thereof may have at least 80%, 85%, 90%, 91%, 92%, 93%, 94%, 95%, 96%, 97, 98, 99%, or 100% (or any percentage in between) identity to SEQ ID NOs: 29, 31, 33, 35, 37, 39, 41, 42, 44, 46, 48 or 49.

Moreover, the LCVR/HCVR pair of the anti-GM2AP antibody of the foregoing embodiment or the antigen-binding fragment thereof may be encoded by the nucleic acid sequence pair having at least 80%, 85%, 90%, 91%, 92%, 93%, 94%, 95%, 96%, 97, 98, 99%, or 100% (or any percentage in between) identity to SEQ ID NOs: 28/29, 30/31, 32/33, 34/35, 36/37, 38/39, 40/41, 40/42, 43/44, 45/46, 47/48, or 50/49, respectively.

In some embodiments, the polynucleotides are substantially identical to those coding for the amino acid sequences as described above. Substantially identical sequences may be polymorphic sequences, i.e., alternative sequences or alleles in a population. Substantially identical sequences may also comprise mutagenized sequences, including sequences comprising silent mutations. A mutation may comprise one or more nucleotide residue changes, a deletion of one or more nucleotide residues, or an insertion of one or more additional nucleotide residues. Substantially identical sequences may also comprise various nucleotide sequences that encode for the same amino acid at any given amino acid position in an amino acid sequence disclosed herein, due to the degeneracy of the nucleic acid code.

For the purposed of this disclosure, a vector comprising the polynucleotides as described above is also provided. Moreover, a host cell comprising the vector as described above is also provided. In some embodiment, the host cell can be a eukaryotic cell, preferably artificially selected or genetically engineered. The eukaryotic cell may comprise, but not be limited to, a Chinese Hamster Ovary (CHO) cell, NSO cell, BHK cell, SP2/0 cell, HEK 293 cell, HEK 293 EBNA cell, PER.C6 cell, COS cell, 239F cell, SF9 cell, SF21 cell and a combination thereof.

In general, the polynucleotides, vectors and host cells comprising the same can be used to generate the anti-GM2AP antibodies or the antigen-binding fragment thereof provided by the aforementioned embodiments. More detailed, the polynucleotides of this embodiment can be, for example, DNA or RNA and may or may not contain intronic sequences. Preferably, the polynucleotides can be a cDNA molecule.

The polynucleotides of this embodiment can be isolated and obtained by any method known in the art. For example, if the nucleotide sequence of an antibody is known, a polynucleotide encoding the antibody may be assembled from chemically synthesized oligonucleotides. This would involve, for example, the synthesis of overlapping oligonucleotides containing portions of the sequence encoding the antibody, annealing and ligating those oligonucleotides, and then amplifying the ligated oligonucleotides by PCR. The disclosed polynucleotides can also be generated from any other suitable source of nucleic acids, such as an antibody cDNA library, or a cDNA library isolated from any tissue or cells expressing the antibody (e.g., from hybridoma cells selected to express an antibody). The cDNAs encoding the light and heavy chains of the anti-GM2AP antibody made by a host cell (e.g., a hybridoma) can be obtained by standard PCR amplification or cDNA cloning techniques. For antibodies obtained from using phage display techniques, the polynucleotides encoding the anti-GM2AP antibodies provided by the aforementioned embodiments can be recovered from various phage clones of the library. In some embodiments, any of the disclosed polynucleotides or isolated nucleic acids may be incorporated into an expression vector. Suitable vectors for expression in various human and animal cell types are known in the art. In some embodiments, host cells are provided comprising the vectors. Suitable host cells include, e.g., a Chinese Hamster Ovary (CHO) cell, NSO cell, BHK cell, SP2/0 cell, HEK 293 cell, HEK 293 EBNA cell, PER.C6 cell, COS cell, 239F cell, SF9 cell, SF21 cell, and/or other human or nonhuman cell lines. In some embodiments, the host cells may transiently or stably express the polynucleotides or the isolated nucleic acids on the vector when cultured in culture medium, thereby providing a method for producing the antibodies or fragments disclosed herein.

Once the DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to an scFv gene. In these manipulations, a $V_L$- or $V_H$-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of mouse and human (or other mammals') heavy chain constant region genes are known in the art (see e.g., Kabat, E. A., et al., (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region. In some embodiments, the heavy chain constant region is selected among IgG1 isotypes. For a Fab fragment heavy chain gene, the VH-encoding DNA can be operatively linked to another DNA molecule encoding only the heavy chain CH1 constant region.

The isolated DNA encoding the $V_L$ region can be converted to a full-length light chain gene (as well as to a Fab light chain gene) by operatively linking the $V_L$-encoding DNA to another DNA molecule encoding the light chain constant region, CL. The sequences of mouse and human (or other mammals') light chain constant region genes are known in the art (see e.g., Kabat, E. A., et al., (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or a lambda constant region.

To create an scFv gene, the $V_H$- and $V_L$-encoding DNA fragments are operatively linked to another fragment encoding a flexible linker, e.g., encoding the amino acid sequence (Gly4-Ser)$_3$ such that the $V_H$ and $V_L$ sequences can be expressed as a contiguous single-chain protein, with the $V_L$ and $V_H$ regions joined by the flexible linker (see e.g., Bird et al., 1988 Science 242:423-426; Huston et at., (1988) Proc. Natl. Acad. Sci. USA 85:5879-5883; McCafferty et al., (1990) Nature 348:552-554).

Kits for Detecting GM2AP

According to one embodiment of the present disclosure, the present application also provides a kit for detecting a GM2-activator protein (GM2AP) in a biological sample. The kit may comprise the anti-GM2AP antibody or the antigen-binding fragment thereof mentioned in the present disclosure. Preferably, the kit of this embodiment may further comprise a substrate and a second antibody which conjugates with a signal generating unit and binds to a Fc domain of the anti-GM2AP antibody or the antigen-binding fragment thereof. The substrate is configured to react with the signal generating unit to generate a signal. Moreover, the kit may further comprise a blocking solution and/or a wash solution. Preferably, the blocking solution may comprise skim milk, bovine serum albumin, or casein and the wash solution may comprise PBS, TBS, PBS including a detergent, or TBS including a detergent.

In some embodiments, the biological sample may comprise whole blood, serum, plasma, urine, or a combination thereof. In addition, the signal generating unit may comprise a radioactive marker, a fluorescent marker, a phosphorescent marker, a chemiluminescent marker or a labeling enzyme. Preferably, the labeling enzyme may comprise a horse radish peroxidase or an alkaline phosphatase.

More preferably, the substrate may be tetramethylbenzidine (TMB) provided that the signal generating unit is a horse radish peroxidase.

Methods for Detecting GM2AP

The present application also provides a method for detecting a GM2-activator protein (GM2AP) in a biological sample by the foregoing anti-GM2AP antibody or the antigen-binding fragment thereof, or more specifically, by the kit of the preceding embodiment. The method of this embodiment may the following steps:
  (a) applying the anti-GM2AP or the antigen-binding fragment thereof mentioned in the present disclosure to said biological sample;
  (b) incubating said biological sample with a secondary antibody conjugated with a detectable label; and
  (c) detecting said detectable label.

For the purpose of the present disclosure, the biological sample may comprise whole blood, serum, plasma, urine, or a combination thereof, and the secondary antibody may bind to a Fc domain of said anti-GM2AP antibody or the antigen-binding fragment thereof. Moreover, the detectable label may comprise an alkaline phosphatase. Meanwhile, the step (c) can be conducted by incubating said detectable label with a p-nitrophenyl phosphate solution and determining an absorbance at $OD_{405}$.

Alternatively, he detectable label may comprises a horse radish peroxidase and the step (c) can be conducted by incubating said detectable label with a tetramethylbenzidine (TMB) solution and determining an absorbance at $OD_{450}$.

Methods for Inducing Anti-GM2AP Antibody or the Antigen-Binding Fragment Thereof The present application also provides a method for inducing any one of the anti-GM2AP antibody or the antigen-binding fragment thereof mentioned in the present disclosure. The method of this embodiment may comprise the following steps:
  (a) administering to a subject a peptide fragment comprising any one of the amino acid sequences of SEQ ID NOs: 1 to 4 listed in Table 1;
  (b) forming hybridoma cells; and
  (c) screening for a hybridoma cell secreting the antibody specifically binding to the glycosylated GM2AP.

Preferably, said peptide fragment of step (a) may comprises the amino acid sequence of SEQ ID NO: 1.

It will be apparent to those skilled in the art that various modifications and variations can be made to the disclosed embodiments. It is intended that the following experimental examples are considered as exemplary only.

Experimental Examples

All materials used in the following experimental examples are commercially available or can be easily obtained by the person with ordinary skills in the art from related commercially available materials without undue experiments.

Production and Purification of GM2AP

In the present application, GM2AP or a peptide fragment of the GM2AP was i.p. injected into BALB/C mice to generate monoclonal antibodies. Specifically, in an embodiment, a peptide fragment of the GM2AP (SEQ ID NO: 1, PIIVPGNVTLSVVG) linked with $(GlcNAc)_2Fuc(Man)_3$ was used to induce antibodies in a test subject, such as mice. In another embodiment, the GM2AP (SEQ ID NO: 2 or SEQ ID NO: 3) linked with $(GlcNAc)_2Fuc(Man)_3$ was used to induce antibodies in a test subject. In still another embodiment, the GM2AP tagged with poly(His), such as eight Histidines, (SEQ ID NO: 4) was used to induce antibodies in a test subject for the convenience of purification. Other tags, such as FLAG, Myc, HA, etc., may be applied as well.

Figure 2:
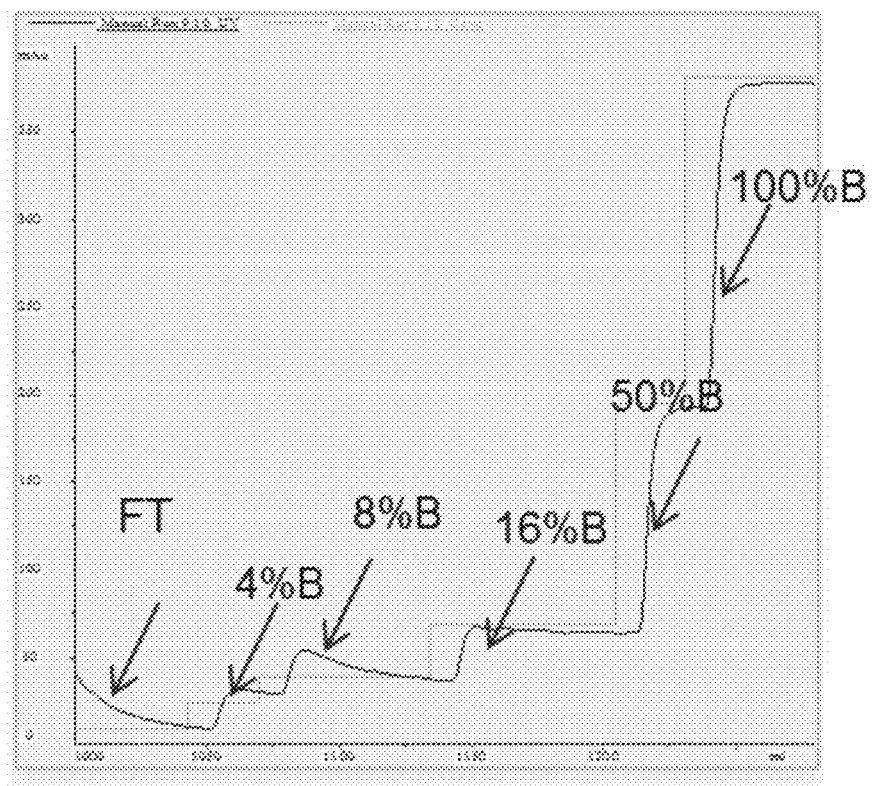
FIG. 2 illustrates (A) collection of the flow-through and the elution of GM2AP-His8, and (B) analysis of the flow-through the elution by coomassie blue.
Figure 2:
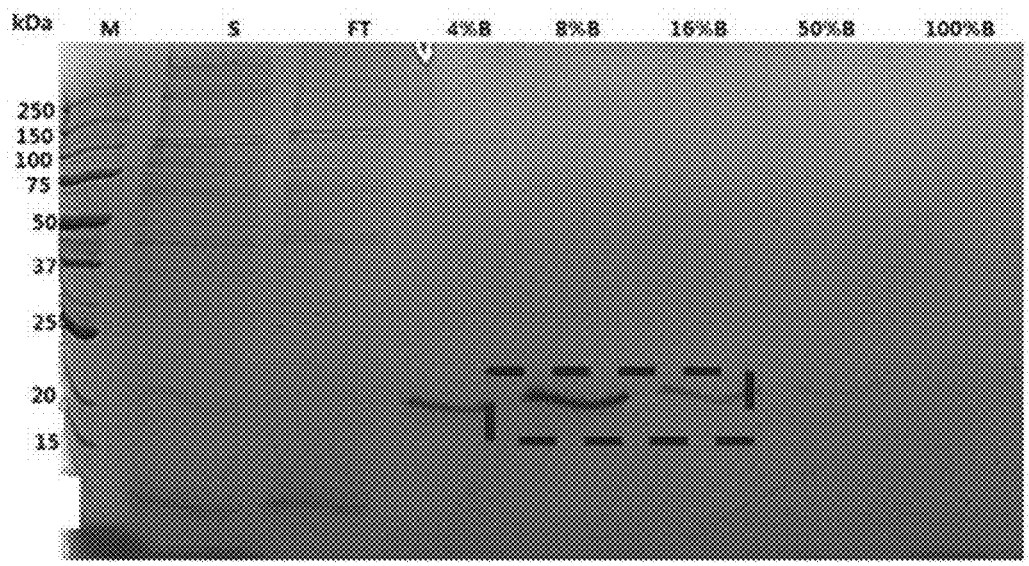

To generate monoclonal antibodies specifically recognizing GM2AP, briefly, the recombinant GM2AP (SEQ ID NO: 4) was expressed in SF9 cells and/or SF21 cells (FIG. 1). The expressed recombinant GM2AP was purified by Ni Excell column (Buffer A: 0.3M NaCl, 25 mM sodium phosphate, 20 mM Imidazole, pH8.0; Buffer B: 0.3M NaCl, 25 mM sodium phosphate, 500 mM Imidazole, pH8.0; dialysis Buffer: 0.3M NaCl, 25 mM sodium phosphate, pH8.0). The SF21 cell lysate was first filtered through 0.22 uM membrane. The Ni Excell column was pre-equilibrated with Buffer A followed by loading the filtered cell lysate onto column. The column was washed with Buffer A and the recombinant GM2AP was eluted from the column with 4%, 8%, 16%, 50% and 100% of buffer B. The 16% and 8% fractions were harvested and dialyzed in dialysis Buffer (FIG. 2).

The purified GM2AP was i.p. injected into BALB/C mice to generate monoclonal antibodies. A titer of the generated anti-GM2AP serum was tested by indirect ELISA. Briefly, GM2A protein (His-tagged) and CD40 (21-193) protein (negative control) were coated on the ELISA plate. Mouse Anti-Histidine Tag mAb (1000×) was used as positive control and normal sera were used as negative control. D56 and D31 pre-bleeding sera were subject to serial dilution and added into the coated wells. Goat Anti-Mouse IgG-HRP (1500×) was used as secondary antibody. The absorbance $OD_{450}$ of the sample mixtures was measured. The results were shown in Tables 4 and 5, and FIG. 3.

Afterwards, the mice were sacrificed and the activated splenocytes were fused with melanoma cells to generate hybridomas. The hybridoma clones which showed the highest affinities to the GM2AP among all were i.p. injected into mice for ascites production to amplify the antibodies. The antibody clones which showed the highest affinity to GM2AP among all were further selected for further investigation, for example, clone No. 21-2B5-F7, 21-2H9-G2, 21-4E3-C8, 21-4B10-E1, 21-4G4-B11, 22-5B1-B2, 22-5F2-E10, 22-4B11-B9, 22-3E6-B11, 22-2E9-G12, etc.

Statistical Analysis

All data were shown as mean±STDEV. The data comparison was determined by unpaired Student t test or ANOVA. The p values less than 0.05 were considered as statistically significant.

Results

Figure 3:
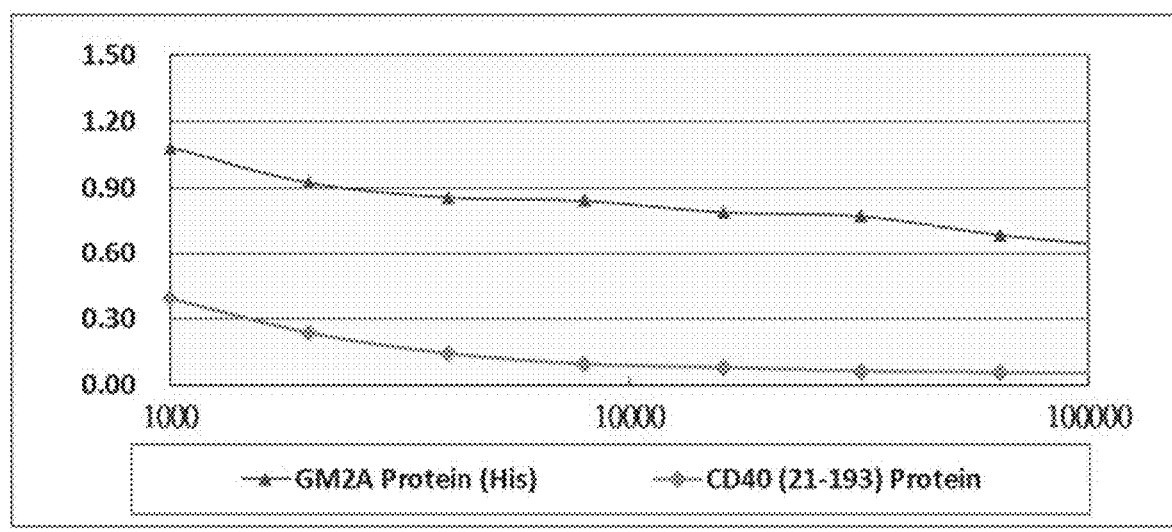
FIG. 3 illustrates the analysis of the serum from the mice immunized by GM2AP by indirect ELISA.

As shown Tables 4 and 5, and FIG. 3, both the D56 and D31 pre-bleeding sera comprises the antibodies specifically binding to GM2AP, instead CD40 (21-193) protein. The presence of anti-GM2AP antibodies was further confirmed by western blot (data not shown).

TABLE 4

| Titer of anti-GM2AP serum_D56 | | |
|---|---|---|
| Mouse No100352622 | GM2AP (His) | CD40 (21-193) Protein |
| positive control (PC) | 1.02 | 1.08 |
| Sera dilution in 1000× | 1.08 | 0.39 |
| Sera dilution in 2000× | 0.92 | 0.24 |
| Sera dilution in 4000× | 0.86 | 0.14 |
| Sera dilution in 8000× | 0.84 | 0.10 |

TABLE 4-continued

Titer of anti-GM2AP serum_D56

| Mouse No100352622 | GM2AP (His) | CD40 (21-193) Protein |
|---|---|---|
| Sera dilution in 16000× | 0.79 | 0.08 |
| Sera dilution in 32000× | 0.77 | 0.06 |
| Sera dilution in 64000× | 0.69 | 0.06 |
| Sera dilution in 128000× | 0.62 | 0.05 |
| Sera dilution in 256000× | 0.52 | 0.05 |
| Sera dilution in 512000× | 0.38 | 0.05 |
| Sera dilution in 1024000× | 0.22 | 0.04 |

TABLE 5

Titer of anti-GM2AP serum_D31

| Mouse No 100352622 | GM2AP (His) | CD40 (21-193) Protein |
|---|---|---|
| positive control (PC) | 1.02 | 1.08 |
| Sera dilution in 1000× | 1.03 | 0.06 |
| Sera dilution in 16000× | 0.54 | 0.05 |
| Sera dilution in 1024000× | 0.12 | 0.05 |

In addition, the antibody clones which showed the highest affinity to GM2AP among all were further selected for further investigation. That is, antibodies of clone No. 21-2B5-F7, 21-2H9-G2, 21-4E3-C8, 21-4B10-E1, 21-4G4-B11, 22-5B1-B2, 22-5F2-E10, 22-4B11-B9, 22-3E6-B11 and 22-2E9-G12 were subject to sequence analysis. The amino acid sequences of the LCVR/HCVR and the corresponding CDRs (LCDR1-3 and HCDR1-3) are shown in Table 2. The nucleic acids sequences encoding the LCVR/HCVR of these monoclonal antibodies are shown in Table 3. In addition, the concentrations of said monoclonal antibodies are listed below.

TABLE 6

Concentration of monoclonal anti-GM2AP antibodies

| No. | Antibody No. | Label Conc. (mg/mL) | Measurement Conc. (mg/mL) |
|---|---|---|---|
| GM1 | 22-5F2-E10 | 3.67 | 3.72 |
| GM2 | 22-5B6-B2 | 3.58 | 3.41 |
| GM3 | 22-4B11-B9 | 3.11 | 3.12 |
| GM4 | 22-3E6-B11 | 3.23 | 3.18 |
| GM5 | 22-2E9-G12 | 3.1 | 3.42 |
| GM6 | 21-4B10-E1 | 3.96 | 4.04 |
| GM7 | 21-4G4-B11 | 2.5 | 2.9 |
| GM8 | 21-2H9-G2 | 3.34 | 3.38 |
| GM9 | 21-4E3-C8 | 2.25 | 2.57 |
| GM10 | 21-2B5-F7 | 2.64 | 2.83 |

Comparison of the Anti-GM2AP Antibodies of the Present Application Between Other Commercial ELISA Kits by Western Blot Assay Four of the antibody clones (21-4B10-E1, 21-4E3-C8, 21-2H9-G2, and 21-2B5-F7) provided by the preceding examples are compared with one commercial anti-GM2AP antibody (Sigma) by Western Blot assay. The assay was carried out by the following steps.

A 12 mL of urine sample obtained from a test subject was centrifuged with a 50 kDa cut-off Centricon centrifugal filter device (Millipore) until the volume of the sample in the upper part is less than 500 μL. Deionized water was added into the upper part to a final volume of 12 mL, followed by centrifugation, until the volume of the sample in the upper part is less than 500 μL. Deionized water was added into the upper part for a second time to a final volume of 12 mL, followed by centrifugation, until the volume of the sample in the upper part is less than 500 μL. The collected sample was subject to desalting and concentration, followed by SDS-PAGE without reducing agent in sample buffer. For the SDS-PAGE, each well was loaded with 25 μL of the collected sample (about 10 μg of protein in amount). The gel after running was transferred to a nitrocellulose (NC) membrane, followed by Western Blot assay stained with four clones of anti-GM2AP antibodies (21-4B10-E1, 21-4E3-C8, 21-2H9-G2, and 21-2B5-F7) provided by the preceding example and the commercial anti-GM2AP antibody (Sigma) as the first antibodies and with suitable secondary anti-Fc antibodies through the standard protocol in the lab. The commercial anti-GM2AP antibody (Sigma) was diluted in 1:1000 before use. The concentrations of the four anti-GM2AP antibodies were summarized in Table 7.

TABLE 7

Concentration of the anti-GM2AP antibodies for Western Blot

| No. | Antibody No. | Conc. (mg/mL) |
|---|---|---|
| GM6 | 21-4B10-E1 | 2.6 |
| GM8 | 21-2H9-G2 | 1.7 |
| GM9 | 21-4E3-C8 | 3.53 |
| GM10 | 21-2B5-F7 | 4.07 |

Figure 4:
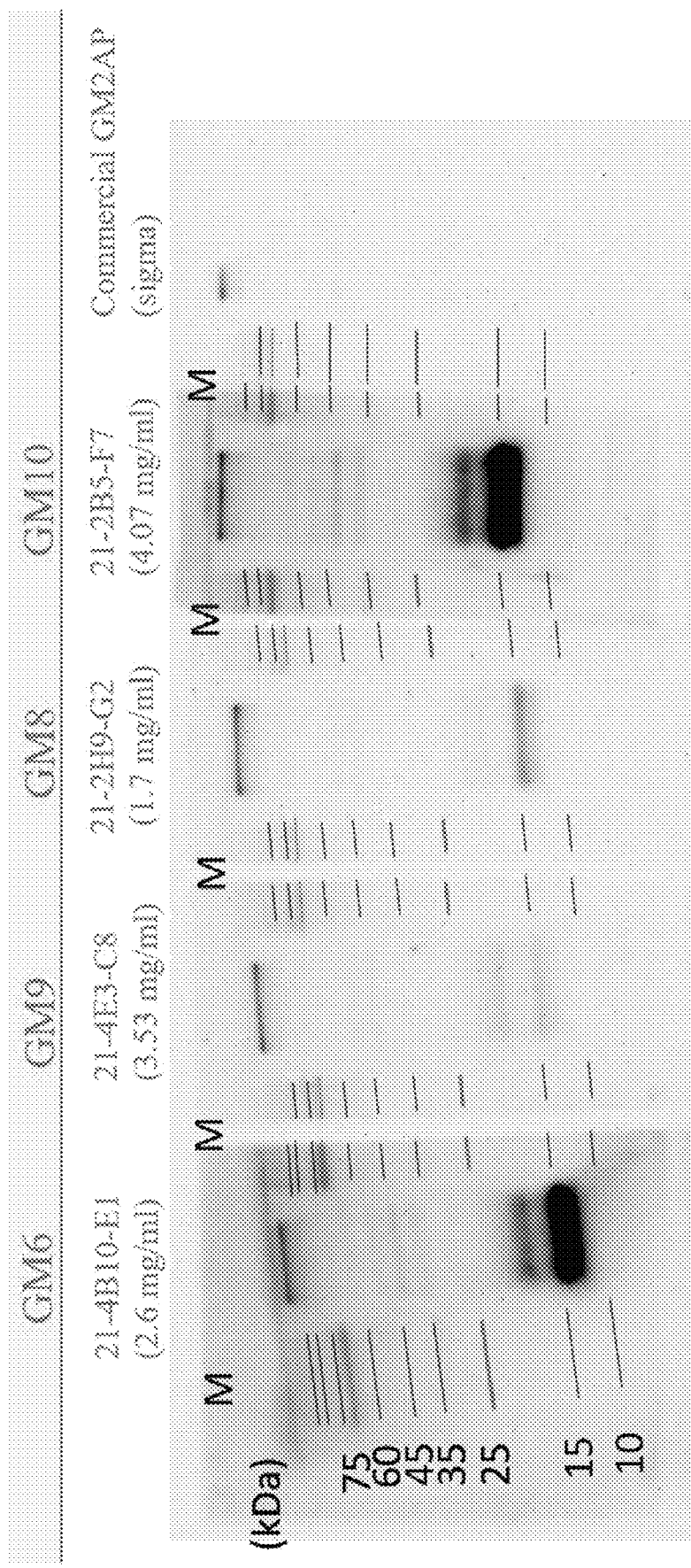
FIG. 4 illustrates the result of the Western Blot assay staining with four anti-GM2AP antibody clones GM6, GM8, GM9 and GM10 and one commercial GM2AP antibody (Sigma).

The result was demonstrated in FIG. 4. As shown in FIG. 4, it was obvious that the GM2AP protein in the urine sample was detected by all of the four anti-GM2AP antibodies clones provided by the preceding examples, whereas such signal was absent from the lane stained with the commercial anti-GM2AP antibody (Sigma).

Sensitivity of the Anti-GM2AP Antibodies by ELISA and SPR Assay

Various fragments (50 ng/well, Table 8) of GM2AP protein with N- or C-terminal biotin modification (C-terminal biotin modified fragments were designated with "(C)") in the wells of streptavidin plates. After incubation under 37° C. for one hour, each well was added with 500 ng/well of first antibodies (GM9=detection antibody; GM10=capture antibody), followed by incubation under 37° C. for another one hour. The secondary antibodies (anti-mouse (HRP), 1:10000 diluted) were added into each well and the plates were incubation under 37° C. for yet another one hour. TMB was added as the substrate and coloring agent for reaction for 5 minutes in the dark. Stop solution was then added to quench the reaction and absorbance at $OD_{450}$ of each well was determined.

TABLE 8

Fragments of VITAEin

| No. | VITAEin |
|---|---|
| 1 | 1-30 (C.) |
| 2 | 1-30 |
| 3 | 21-50 |
| 4 | 41-70 |
| 5 | 61-90 |
| 6 | 81-110 |
| 7 | 121-149 (C.) |
| 8 | 121-150 |

TABLE 8-continued

Fragments of VITAEin

| No. | VITAEin |
|---|---|
| 9 | 141-170 |
| 10 | 161-193 |

Figure 5:
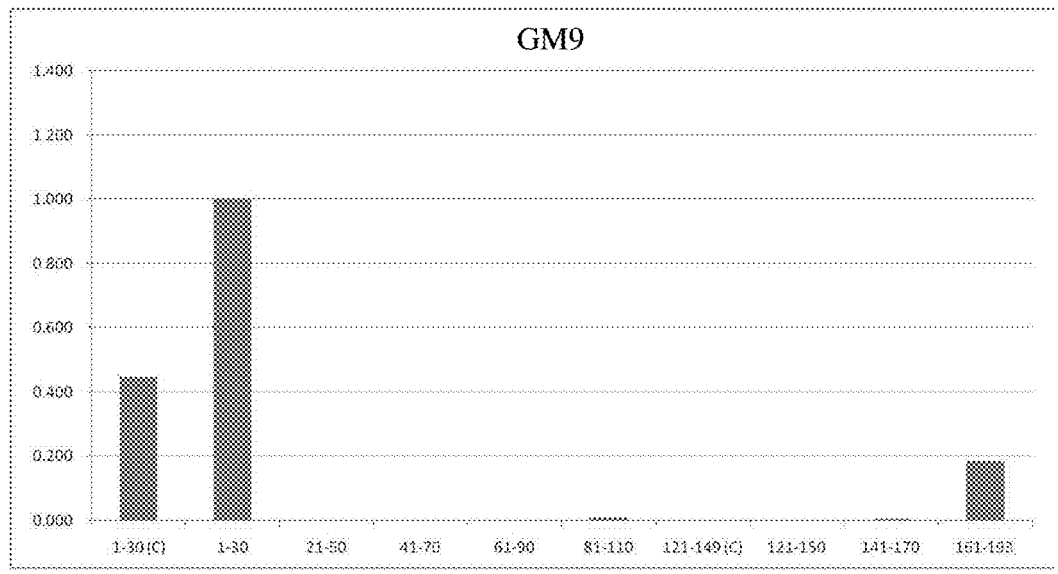
FIG. 5 illustrates that GM9 recognizes various fragments of VITAEin protein.
Figure 6:
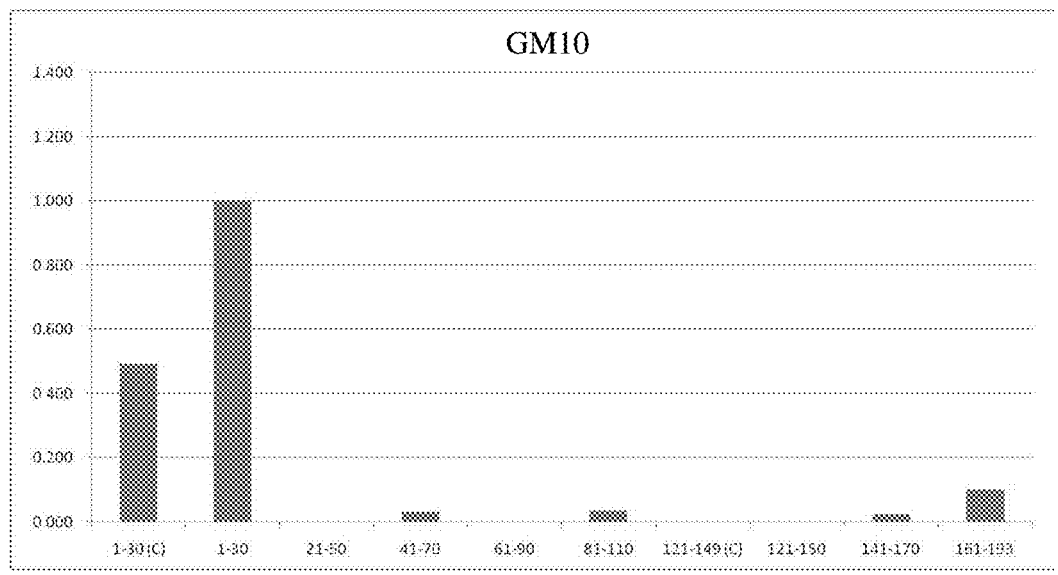
FIG. 6 illustrates that GM10 recognized various fragments of VITAEin protein.

As shown in FIGS. 5 and 6, GM9 and GM10 recognized the portion of VITAEin 1-30 significantly and the portion of GM2AP 170-193 mildly. After structural analysis (data not shown), VITAEin 1-30 and VITAEin 170-193 were positioned closely in structure. Hence, it is inferred that the antibodies can recognize the portion of VITAEin 1-30 and also recognize both the portions of VITAE1-30 and VITAEin 170-193 in spatial. VITAEin 1-30 and VITAE 170-193 were subject to Protein BLAST on NCBI. Non-VITAEin proteins were not present in the top 100 hits of the result. Hence, the antibodies were demonstrated to have high specificity toward the recognizing regions.

Moreover, the GM9 and GM10 antibody pair (GM10=capture; GM9=detection) were analyzed for their $k_a$ ($M^{-1}s^{-1}$), $k_d$ ($s^{-1}$) and $K_D$ (M) values by Surface plasmon resonance (SPR) assay with GE BIAcore 3000 instrument, as summarized in Table 9.

TABLE 9

$K_D$ values of the anti-GM2AP antibodies

| Ab | $k_a$ ($M^{-1}s^{-1}$) | $k_d$ ($s^{-1}$) | $K_D$ (M) |
|---|---|---|---|
| GM9 | 3.26E5 | 4.09E−5 | 1.25E−10 |
| GM10 | 2.1E5 | 1.9E−4 | 8.8E−10 |

From the Table 9, GM9 and GM10 were demonstrated to have a $K_D$ of 1.25E-10 M and 8.8E-10 M by SPR assay, respectively. Hence, the antibodies GM9 and GM10 were demonstrated to have an high affinity toward the antigen and were difficult to dissociated from the antigen.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

I claim:

1. A recombinant antibody or the antigen-binding fragment thereof which specifically binds GM2-activator protein (GM2AP), wherein the recombinant antibody or the antigen-binding fragment thereof comprises:
   a light chain variable region (LCVR) comprising three light chain complementary determining region (LCDR1-3) amino acid sequences, wherein LCDR1 is SEQ ID NO: 57, LCDR2 is SEQ ID NO: 58, and LCDR3 is SEQ ID NO: 59; and
   a heavy chain variable region (HCVR) comprising three heavy chain complementary determining region (HCDR1-3) amino acid sequences, wherein HCDR1 is SEQ ID NO: 66, HCDR2 is SEQ ID NO: 67, and HCDR3 is SEQ ID NO: 68.

2. The recombinant antibody or the antigen-binding fragment thereof according to claim 1, wherein the LCVR comprises an amino acid sequence consisting of SEQ ID NO: 7.

3. The recombinant antibody or the antigen-binding fragment thereof according to claim 2, wherein the HCVR comprises an amino acid sequence consisting of SEQ ID NO: 10.

4. The recombinant antibody or the antigen-binding fragment thereof according to claim 1, wherein the recombinant antibody or the antigen-binding fragment thereof is selected from the group consisting of a diabody, a Fab, a Fab', a F(ab')$_2$, an Fv fragment, a disulfide stabilized Fv fragment (dsFv), a (dsFv)$_2$, a bispecific dsFv (dsfv-dsfv'), a disulfide stabilized diabody (ds diabody), a single-chain antibody molecule (scfv), an scfv dimer (bivalent diabody) and any combination thereof.

5. The recombinant antibody or the antigen-binding fragment thereof according to claim 1, wherein the recombinant antibody or the antigen-binding fragment thereof is selected from the group consisting of a monoclonal antibody, multispecific antibody, humanized antibody, chimeric antibody and any combination thereof.

6. A polynucleotide encoding the recombinant antibody or the antigen-binding fragment thereof according to claim 1, comprising a nucleic acid sequence which is selected from the group consisting of SEQ ID NOs: 30 and 33.

7. The polynucleotide according to claim 6, wherein the nucleic acid sequence encoding the LCVR is SEQ ID NO: 30.

8. The polynucleotide according to claim 7, wherein the nucleic acid sequence encoding the HCVR is SEQ ID NO: 33.

9. A method for detecting a GM2-activator protein (GM2AP) in a biological sample, comprising:
   (a) applying the recombinant antibody or the antigen-binding fragment thereof according to claim 1 to said biological sample;
   (b) incubating said biological sample with a secondary antibody conjugated with a detectable label; and
   (c) detecting said detectable label.

10. The method according to claim 9, wherein the biological sample comprises whole blood, serum, plasma, urine, or a combination thereof.

11. The method according to claim 9, wherein the secondary antibody binds to a Fc domain of the antibody or the antigen-binding fragment thereof.

12. The method according to claim 9, wherein the detectable label comprises an alkaline phosphatase.

13. The method according to claim 9, wherein the step (c) is conducted by incubating said detectable label with a p-nitrophenyl phosphate solution and determining an absorbance at $OD_{405}$.

14. The method according to claim 9, wherein the step (c) is conducted by incubating said detectable label with a tetramethylbenzidine (TMB) solution and determining an absorbance at $OD_{450}$.

* * * * *